(12) United States Patent
Stack et al.

(10) Patent No.: US 11,129,603 B2
(45) Date of Patent: *Sep. 28, 2021

(54) GUIDEWIRELESS TRANSSEPTAL DELIVERY SYSTEM FOR THERAPEUTIC DEVICES OF THE AORTIC VALVE

(71) Applicant: Synecor LLC, Durham, NC (US)

(72) Inventors: Richard S Stack, Chapel Hill, NC (US); William L. Athas, Chapel Hill, NC (US); Kevin W. Johnson, Durham, NC (US)

(73) Assignee: Synecor LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/365,601

(22) Filed: Mar. 26, 2019

(65) Prior Publication Data
US 2021/0077084 A1    Mar. 18, 2021

Related U.S. Application Data

(63) Continuation-in-part of application No. PCT/US2017/062913, filed on Nov. 22, 2017, and a
(Continued)

(51) Int. Cl.
*A61B 17/00* (2006.01)
*A61M 25/01* (2006.01)
*A61F 2/24* (2006.01)

(52) U.S. Cl.
CPC ...... *A61B 17/00234* (2013.01); *A61F 2/2427* (2013.01); *A61M 25/0125* (2013.01);
(Continued)

(58) Field of Classification Search
CPC .... A61B 17/00234; A61B 2017/00243; A61B 2017/00323; A61B 2017/00358; A61M 25/0125; A61F 2/2427
See application file for complete search history.

(56) References Cited

U.S. PATENT DOCUMENTS 5,190,050 A  3/1993 Nitzsche
5,658,263 A  8/1997 Dang et al.
(Continued)

FOREIGN PATENT DOCUMENTS

EP  1534374 B1  1/2007
EP  1807143 A1  7/2007
(Continued)

OTHER PUBLICATIONS

Sondergaard,Lars et al, First-in-Human Case of Transfemoral CardiAQ Mitral Valve Implantation, Circ. Cardiovasc Interv. 2015.
(Continued)

*Primary Examiner* — Anh T Dang

(57) ABSTRACT

A system and method used to deliver an aortic valve therapeutic device to an aortic valve site includes a cable percutaneously introduced a cable into a vasculature of a patient and positioned to run from a femoral vein, through the heart via a transeptal puncture, and to a femoral artery. The therapeutic device is passed over an end of the cable at the venous side and is secured to the cable. The therapeutic device is pushed in a distal direction while the second end of the cable is pulled in the proximal direction to advance the therapeutic device to the mitral valve site. A left ventricle redirector aids in orienting the therapeutic device and preventing migration of the cable towards delicate mitral valve structures and chordae tendoneae during advancement of the therapeutic device.

23 Claims, 38 Drawing Sheets

Related U.S. Application Data continuation-in-part of application No. PCT/US2018/045445, filed on Aug. 6, 2018.

(60) Provisional application No. 62/647,894, filed on Mar. 26, 2018, provisional application No. 62/541,761, filed on Aug. 6, 2017, provisional application No. 62/567,736, filed on Oct. 3, 2017, provisional application No. 62/541,771, filed on Aug. 6, 2017.

(52) U.S. Cl.
CPC ............ *A61B 2017/00243* (2013.01); *A61B 2017/00323* (2013.01); *A61B 2017/00358* (2013.01)

(56) References Cited

U.S. PATENT DOCUMENTS

| | | | |
|---|---|---|---|
| 5,873,842 A | 2/1999 | Brennen et al. | |
| 6,004,280 A | 12/1999 | Buck et al. | |
| 6,183,463 B1 | 2/2001 | Webster, Jr. | |
| 6,475,195 B1 | 11/2002 | Voda | |
| 6,592,581 B2 | 7/2003 | Bowe | |
| 6,613,046 B1 | 9/2003 | Jenkins et al. | |
| 7,056,314 B1 | 6/2006 | Florio et al. | |
| 7,115,134 B2 | 10/2006 | Chambers | |
| 7,481,805 B2 | 1/2009 | Magnusson | |
| 7,647,124 B2 | 1/2010 | Williams | |
| 7,729,782 B2 | 6/2010 | Williams et al. | |
| 8,096,985 B2 | 1/2012 | Legaspi et al. | |
| 8,235,916 B2 | 8/2012 | Whiting et al. | |
| 8,435,227 B2 | 5/2013 | Takagi et al. | |
| 8,606,369 B2 | 12/2013 | Williams et al. | |
| 8,827,982 B2 | 9/2014 | Goode et al. | |
| 8,926,588 B2 | 1/2015 | Berthiaume et al. | |
| 8,996,135 B2 | 3/2015 | Elencwajg | |
| 9,072,872 B2 | 7/2015 | Asleson et al. | |
| 9,078,994 B2 | 7/2015 | Rosenman et al. | |
| 9,173,646 B2 | 11/2015 | Fabro | |
| 9,220,874 B2 | 12/2015 | Pillai et al. | |
| 9,320,564 B2 | 4/2016 | Avitall et al. | |
| 9,511,205 B2 | 12/2016 | Inoue | |
| 9,616,197 B2 | 4/2017 | Serina et al. | |
| 9,814,814 B2 | 11/2017 | Corbett et al. | |
| 10,105,221 B2 | 10/2018 | Siegel | |
| 2001/0005789 A1* | 6/2001 | Root .............. | A61B 18/24 606/200 |
| 2004/0003819 A1* | 1/2004 | St. Goar .............. | A61B 17/122 128/898 |
| 2004/0127847 A1 | 7/2004 | DuBois | |
| 2006/0089618 A1 | 4/2006 | McFerran et al. | |
| 2006/0155158 A1 | 7/2006 | Aboul-Hosn | |
| 2006/0167535 A1 | 7/2006 | Johnson | |
| 2006/0217794 A1 | 9/2006 | Ruiz et al. | |
| 2007/0032850 A1 | 2/2007 | Ruiz et al. | |
| 2007/0049906 A1 | 3/2007 | Magnusson | |
| 2007/0060914 A1 | 3/2007 | Magnusson | |
| 2007/0100299 A1 | 5/2007 | Magnusson | |
| 2007/0112422 A1 | 5/2007 | Dehdashtian | |
| 2007/0156233 A1 | 7/2007 | Kapadia et al. | |
| 2007/0299403 A1 | 12/2007 | Crowe et al. | |
| 2010/0114306 A1 | 5/2010 | Lenihan et al. | |
| 2010/0160725 A1 | 6/2010 | Kiser et al. | |
| 2010/0185172 A1 | 7/2010 | Fabro | |
| 2010/0198056 A1 | 8/2010 | Fabro et al. | |
| 2010/0198192 A1 | 8/2010 | Serina et al. | |
| 2010/0198208 A1 | 8/2010 | Napp et al. | |
| 2010/0249491 A1 | 9/2010 | Farnan et al. | |
| 2011/0022057 A1 | 1/2011 | Eigler et al. | |
| 2012/0041422 A1 | 2/2012 | Whiting et al. | |
| 2012/0101442 A1 | 4/2012 | Legaspi et al. | |
| 2012/0172656 A1 | 7/2012 | Walters et al. | |
| 2014/0107399 A1 | 4/2014 | Spence | |
| 2014/0276395 A1* | 9/2014 | Wilson .............. | A61M 25/0141 604/95.04 |
| 2014/0276782 A1 | 9/2014 | Paskar | |
| 2014/0276904 A1 | 9/2014 | Hanson et al. | |
| 2014/0303719 A1* | 10/2014 | Cox ............ | A61F 2/2466 623/2.11 |
| 2014/0371719 A1 | 12/2014 | Carnevale | |
| 2015/0258312 A1 | 9/2015 | Tuseth | |
| 2015/0273136 A1 | 10/2015 | Osiev | |
| 2015/0305864 A1 | 10/2015 | Quadri et al. | |
| 2015/0328382 A1 | 11/2015 | Corbett et al. | |
| 2016/0022961 A1 | 1/2016 | Rosenman et al. | |
| 2016/0066993 A1 | 3/2016 | Avitall et al. | |
| 2016/0074623 A1 | 3/2016 | Pillai et al. | |
| 2016/0158506 A1* | 6/2016 | Eliasen ............ | A61M 39/22 604/509 |
| 2016/0213472 A1* | 7/2016 | Kim .............. | A61F 2/2451 |
| 2016/0220785 A1 | 8/2016 | Fabro | |
| 2016/0317288 A1 | 11/2016 | Rogers et al. | |
| 2016/0317289 A1* | 11/2016 | Tozzi ............ | A61F 2/246 |
| 2017/0224483 A1 | 8/2017 | Kizuka | |
| 2017/0245988 A1 | 8/2017 | Siegel et al. | |
| 2017/0258614 A1 | 9/2017 | Griffin | |
| 2017/0361065 A1 | 12/2017 | Legaspi et al. | |
| 2018/0043132 A1 | 2/2018 | Serina et al. | |
| 2018/0078370 A1 | 3/2018 | Kovalsky et al. | |
| 2018/0104398 A1 | 4/2018 | Corbett et al. | |
| 2018/0311421 A1 | 11/2018 | Tuseth et al. | |
| 2018/0318079 A1 | 11/2018 | Patel et al. | |
| 2019/0117937 A1 | 4/2019 | Humphrey et al. | |
| 2019/0151614 A1 | 5/2019 | Hsueh et al. | |

FOREIGN PATENT DOCUMENTS

| | | |
|---|---|---|
| EP | 2687254 B1 | 4/2015 |
| EP | 2913080 A2 | 9/2015 |
| EP | 3142721 A1 | 3/2017 |
| EP | 3288491 A1 | 3/2018 |
| EP | 3302363 A1 | 4/2018 |
| WO | 200060995 A2 | 10/2000 |
| WO | 2005037345 A2 | 4/2005 |
| WO | 2006052651 A1 | 5/2006 |
| WO | 2007149974 A2 | 12/2007 |
| WO | 2008012914 A1 | 1/2008 |
| WO | 2009137712 A1 | 11/2009 |
| WO | 2010085456 A1 | 7/2010 |
| WO | 2010085457 A1 | 7/2010 |
| WO | 2012178115 A2 | 12/2012 |
| WO | 2013181397 A1 | 12/2013 |
| WO | 2014065714 A2 | 5/2014 |
| WO | 2014138482 A1 | 9/2014 |
| WO | 2014197962 A1 | 12/2014 |
| WO | 2015175718 A1 | 11/2015 |
| WO | 2016176409 A1 | 11/2016 |
| WO | 2016196933 A1 | 12/2016 |
| WO | 2017139246 A1 | 8/2017 |
| WO | 2017155892 A1 | 9/2017 |
| WO | 1994003227 A1 | 4/2018 |
| WO | 2018098210 A1 | 5/2018 |
| WO | 2019055154 A2 | 3/2019 |

OTHER PUBLICATIONS

International Search Report and Written Opinion for PCT/US2017/062913 dated Feb. 8, 2018.
International Search Report and Written Opinion for PCT/US2020/017370 dated Nov. 6, 2020.

* cited by examiner

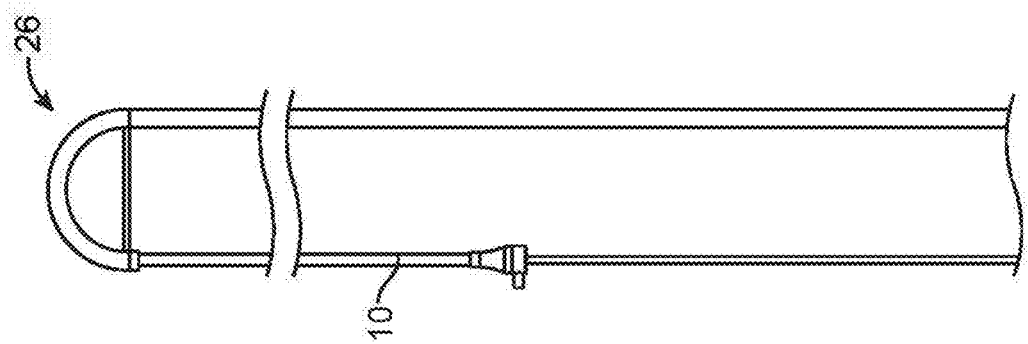
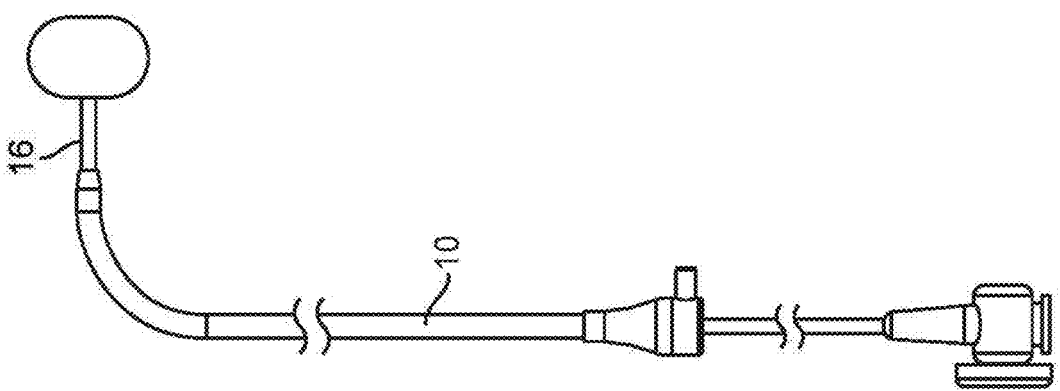
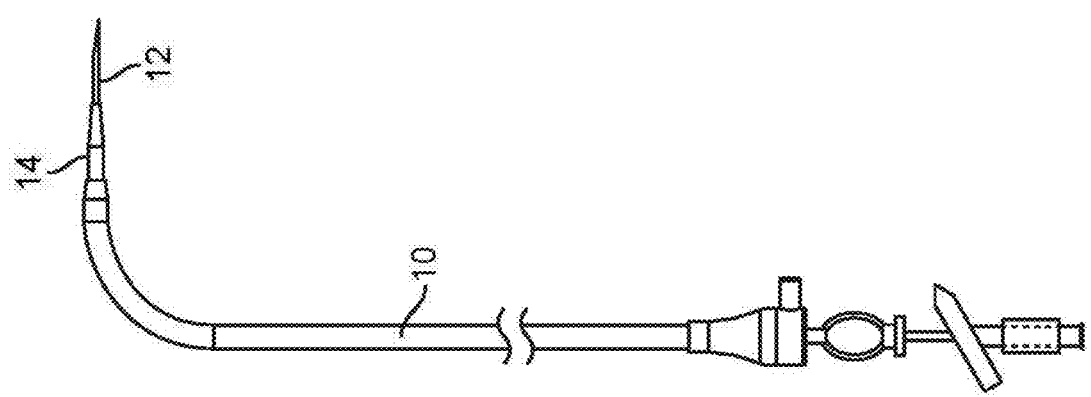
FIG. 1A
FIG. 1B
FIG. 1C

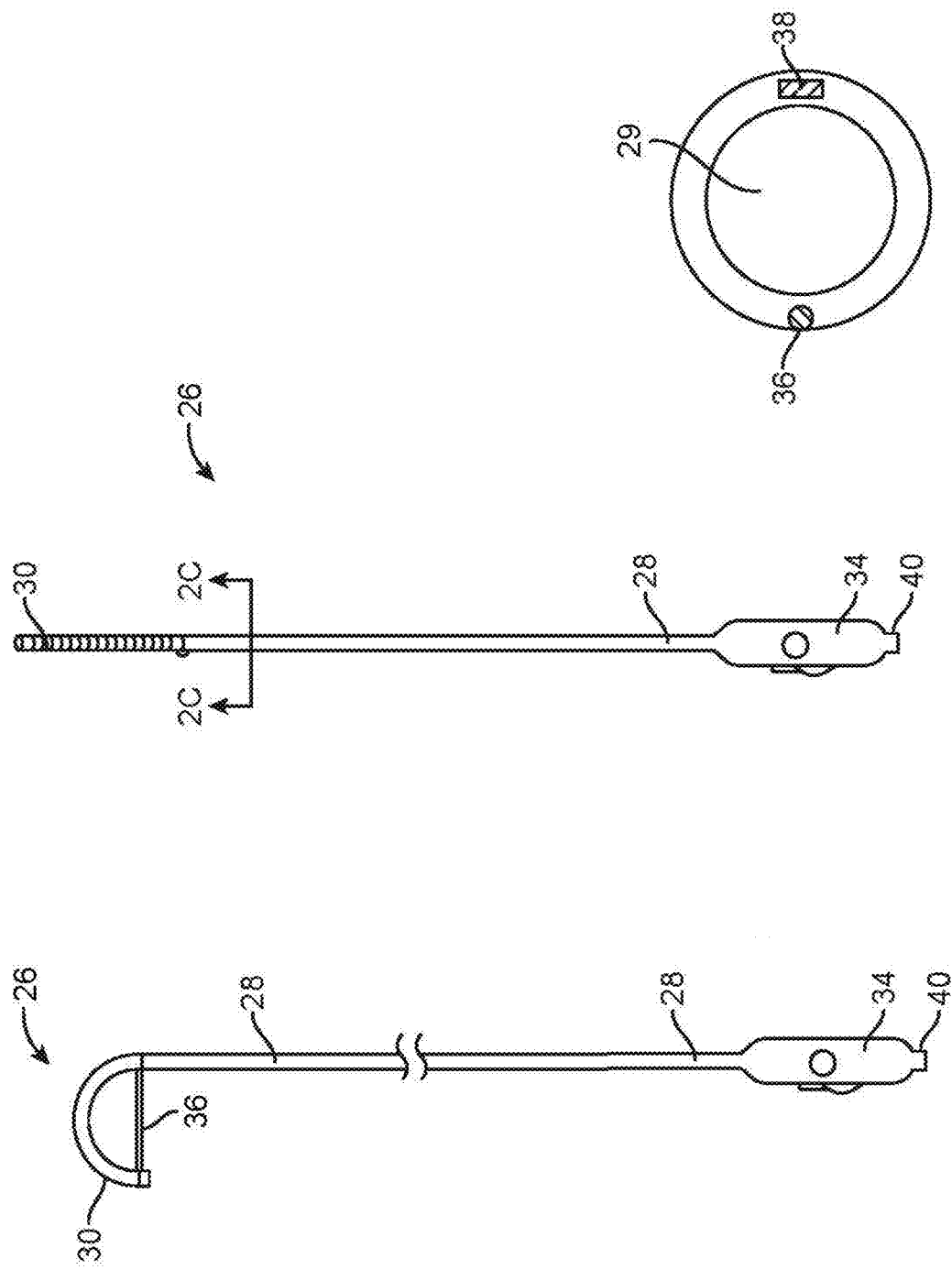

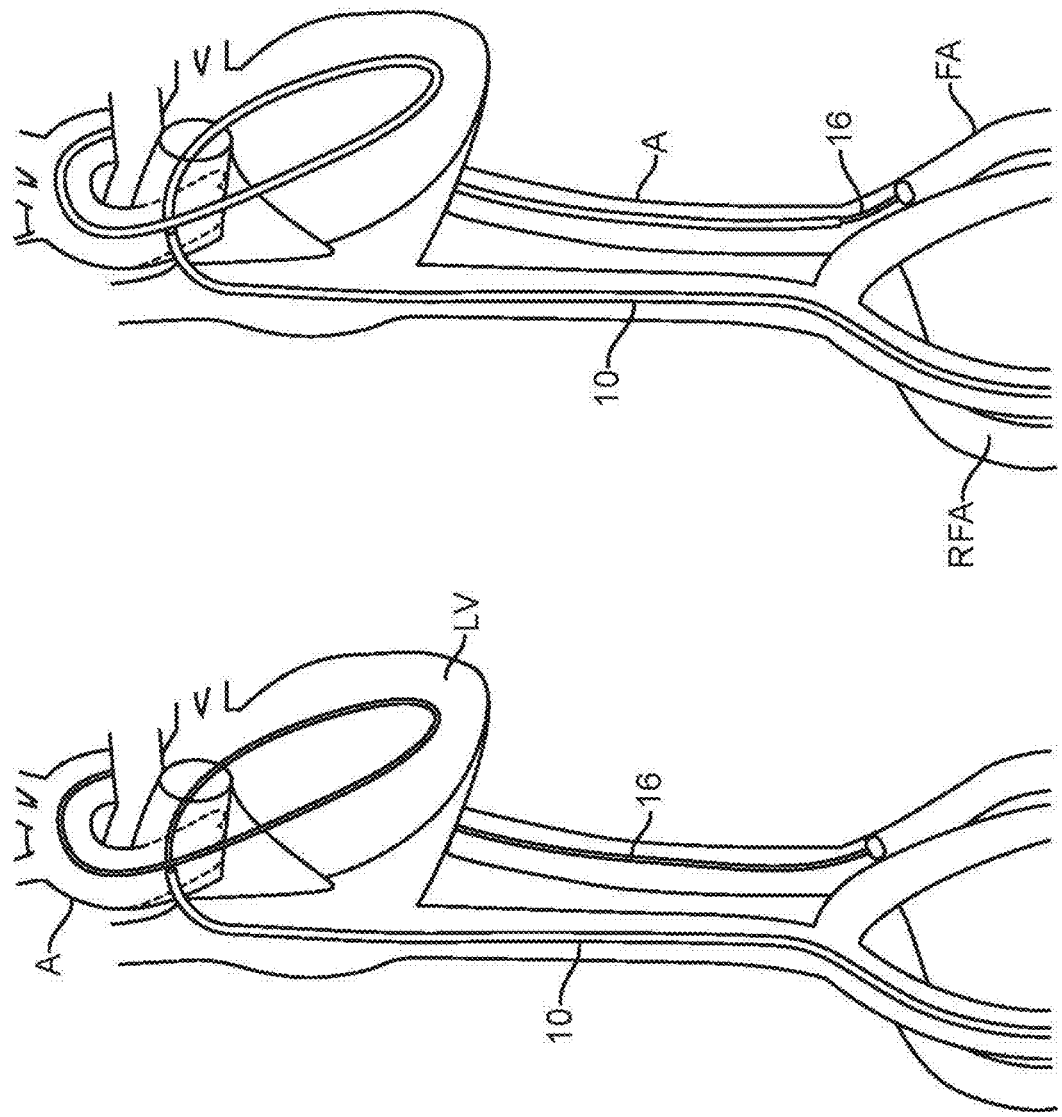

GUIDEWIRELESS TRANSSEPTAL DELIVERY SYSTEM FOR THERAPEUTIC DEVICES OF THE AORTIC VALVE

This application claims the benefit of U.S. Provisional Application 62/647,894, filed Mar. 26, 2018, and is a continuation in part of PCT/US17/62913, filed Nov. 22, 2017. This application is also a continuation in part of PCT/US18/045445, filed 6 Aug. 2018, which claims the benefit of U.S. Provisional Applications 62/541,761, filed Aug. 6, 2017, U.S. 62/541,771, filed Aug. 6, 2017, U.S. 62/567,736, filed Oct. 3, 2017, and U.S. 62/647,894, filed Mar. 26, 2018. Each of these applications is fully incorporated herein by reference.

BACKGROUND

A system that is used for transeptally driving mitral valve therapeutic devices into place is described in Applicant's co-pending PCT Application No. PCT/US17/62913 (Ref: ATR-820). A modified version of that system and method are described herein for use in implanting an aortic valve therapeutic device, such as an aortic valve replacement device or a device for repairing an aortic valve. The method described below and illustrated in the attached drawings differs from that described in PCT/US17/62913 primarily in that the aortic valve therapeutic device, once positioned in the left ventricle, is then advanced to the native aortic valve location.

BRIEF DESCRIPTION OF THE DRAWINGS

FIG. 1A is a side elevation view of a Right-to-Left conduit ("RLC") assembled with a Brockenbrough needle and dilator.

FIG. 1B is a side elevation view of the RLC of FIG. 1A assembled with a tracker balloon catheter.

FIG. 1C is a side elevation view of the RLC of FIG. 1A assembled with a Left Ventricle Redirector ("LVR").

FIG. 2A is a side elevation view of the LVR with the distal end in the curved position to deploy the protective panel.

FIG. 2B is a side elevation view of the LVR with the distal end in the straight position.

FIG. 2C is a cross-section view of the shaft of the LVR taken along the plane designated 2C-2C in FIG. 2B.

FIG. 4B shows the tip of the RLC in the left atrium following removal of the needle assembly;

FIGS. 7-12 are schematic depicting the tracker balloon being carried by the flow of blood from the left atrium, into and through the aorta, to the femoral artery.

FIGS. 13-14 shows advancement of the RLC over the tracker balloon shaft and withdrawal of the balloon catheter from the RLC.

As shown in FIG. 23, the dilator may be advanced over the cable and have its tapered tip inserted into the RLC. Then, as shown in FIG. 24, the LVR may be advanced over the dilator to the RLC.

FIGS. 28A through 29C show a TAVR system being advanced over the cable from the venous side. More particularly, FIGS. 28A and 28B show the TAVR system advancing through the inferior vena cava, and FIGS. 29A through 29C show the TAVR system passing through the right atrium to the septum.

DETAILED DESCRIPTION

Figure 3A:
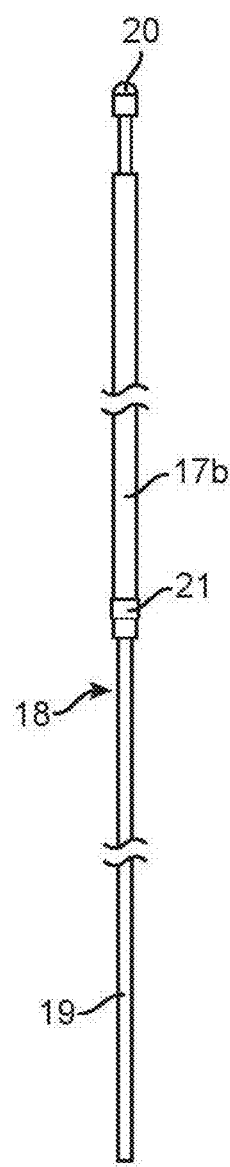
FIG. 3A is an elevation view of the cable.

A system and method are described herein for use in moving an aortic valve therapeutic device ("AVTD") into position for treating an aortic valve. The presently disclosed system is designed to aid in the delivery of an AVTD to an aortic valve location. The terms "aortic valve therapeutic device" or "AVTD" used here refer to any device that may be delivered to the native aortic valve site for a therapeutic purpose. In the description that follows, the AVTD is shown as an aortic valve delivery system carrying a replacement aortic valve for a TAVR procedure, but it should be understood that the system and method described may be used to deliver other types of AVTD's such as those used to repair an aortic valve.

As will be appreciated from a review of the more detailed discussion that follows, the cable system functions to both push the proximal end of the AVTD while simultaneously pulling on the distal nose of it with equal and coordinated force to drive the AVTD across the interatrial septum. Pulling down further on the distal nose of the AVTD using the cable provides a steering force that serves to direct the stiff, bulky AVTD into position across the interatrial septum, and into the left atrium. The AVTD is further advanced through the center of the mitral valve at an angle that is perpendicular to the MV plane by use of a steering mechanism present in a unique device referred to as the LV redirector (described in detail below). From the left ventricle, the AVTD are moved, while remaining in contact with one another, towards the native aortic valve site until the AVTD is positioned at that site.

In the description of system and method below, the access points for the components of the system are described as the right femoral vein for the venous access and the left femoral artery for the arterial access. However, the system and method can just as readily be used with a different combination of venous and arterial access. For example, venous access may be gained via the right femoral vein and arterial access may be gained via the right femoral artery. Alternatively, both access points may be on the left side. In yet another embodiment, venous access is gained via the left femoral vein and arterial access is gained via the right femoral artery.

System

Referring to FIG. 1A, the system includes a Right-to-Left conduit 10 ("RLC"), an elongate tubular catheter having a length sufficient to permit it to extend from the right femoral vein of a human adult to the right atrium, across the interatrial septum to the left atrium, through the aorta and into the femoral artery on the patient's left or right side. The RLC 10 includes a distal portion shape set into a curved configuration to help orient the needle used for transeptal puncture towards the interatrial septum. In alternative embodiments the RLC may be steerable using pullwires or alternative means. The durometer of the RLC is relatively low (eg 55 D) as known in the art for cardiovascular catheters so as to minimize tissue trauma, although a significant length on the proximal part of the catheter is formed of a higher durometer (e.g. 70 D) to give the conduit sufficient column strength to avoid buckling when used to push during advancement of the LVR as described below. This higher durometer section may be the part of the conduit that, when the conduit fully extends between the right femoral vein and right or left femoral artery, begins at or near the proximal end of the conduit and terminates within the inferior vena, and may be as much as a third of the length of the RLC. In FIG. 1A, the RLC 10 is shown assembled with a Brockenbrough needle assembly 12 and dilator 14 for use in the transeptal catheterization step of the method.

The system further includes a tracker balloon catheter 16, shown extending through the RLC 10 in FIG. 1B, comprising an inflatable balloon on the distal end of the catheter. The balloon catheter 16 includes a guidewire lumen. The balloon may be inflated with a fluid or gas, including CO2 or saline, or it may be a self-expanding "vacuum balloon."

In FIG. 1C, the RLC 10 is shown assembled with a conveyor cable 18 and a left ventricle redirector or "LVR" 26. Details of the LVR can be seen in FIGS. 2A-2C. The LVR includes an elongate catheter shaft 28 having a proximal handle 32 with a luer port 40. As shown in the cross-section view of FIG. 2C. The shaft includes a lumen 29 accessible via the port 40. This lumen extends to the distal tip of the shaft. Incorporated within the wall of the LVR shaft are a pullwire 26 and a return wire 38. The pullwire exits the sidewall of the shaft 28 near the shaft's distal end, runs along the exterior of the shaft, and is affixed to the distal end of the shaft. Increasing tension on the pullwire 26 pulls the distal end of the shaft into a curve as shown in FIG. 2A. The handle 32 includes actuators to actuate the pull wire to bend the shaft and to actuate the return wire to return the distal end of the shaft to the generally straight configuration (as in FIG. 2B). The return wire 38 may have a rectangular diameter as shown, with the long edges oriented to aid in preferential bending of the catheter.

A membrane 30 is positioned along a portion of the distal part of the shaft and along the external portion of the pullwire 26. When the pullwire is relaxed and the shaft is in the straight configuration, the panel and pull wire run along the distal part of the shaft. The membrane forms the D-shaped barrier shown in FIG. 2A when the distal end is drawn into the curved configuration by action of the pullwire. The barrier forms a protective panel extending between the external part of the pullwire and the shaft 28, substantially eliminating gaps between the two. The panel may be made of an elastomeric polymer or other material.

Note that the term "pullwire" is not intended to mean that the pullwires must be formed of wire, as that term is used more broadly in this application to represent any sort of tendon, cable, or other elongate element the tension on which may be adjusted to change the shape of the LVR or other catheter in which the pullwire is used.

The conveyor cable 18, shown in FIG. 3A comprises an elongate cable having distal cable section 17a having a broadened distal tip 20 such as the ball tip feature shown in the drawings. The tip 20 may include a distal face having convex curvature and a cylindrical proximal part with a generally flat proximal face to facilitate engagement using a snare. A larger diameter intermediate section 17b is proximal to the distal section 17a and includes a polymer coating. A proximal section 19 comprises a stiff mandrel proximal to the intermediate section 17a. The proximal section is sufficiently stiff to give column support for pushing of the cable during the RLC removal discussed below. A radiopaque marker band 21 is positioned between the proximal mandrel section 19 and the intermediate section 17b. When the cable 18 is assembled with the segmental tensioner 22 (discussed below), the soft distal tip of the segmental tensioner mates with the marker band 21, allowing the user to see on the fluoroscopic image the transition between the segmental tensioner and the intermediate (coated) section 17b of the cable.

Figure 3B:
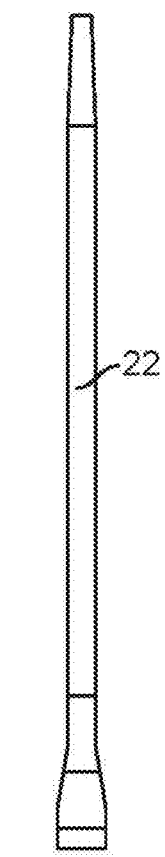
FIG. 3B is an elevation view of the tensioner.
Figure 3C:
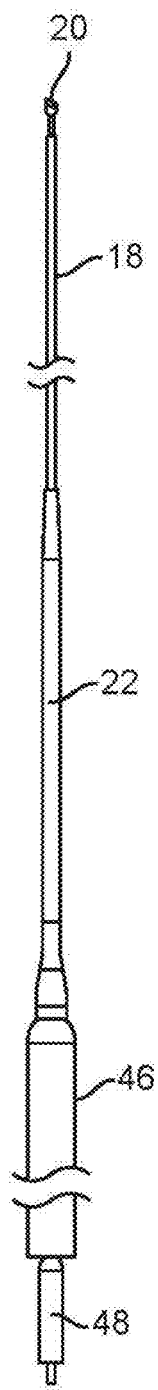
FIG. 3C shows an assembly of the cable, tensioner, MVTD and a cable lock.

Segmental tensioner 22, shown in FIG. 3B, is a short length (e.g. 30-35 mm) tubular component having a flexible tip section (e.g. 40 D) and a more rigid (e.g. 70 D) proximal hub section of broader diameter. The inner diameter of the hub section is proportioned to receive the distal tip of the AVTD. The segmental tensioner incorporates a deadstop within the shaft inner diameter to engage the polymer coated intermediate section 17b of the conveyor cable and to lock the AVTD 46 in position, preventing it from advancing independently of the conveyor cable as it is moved towards the mitral valve.

Method

Figure 4A:
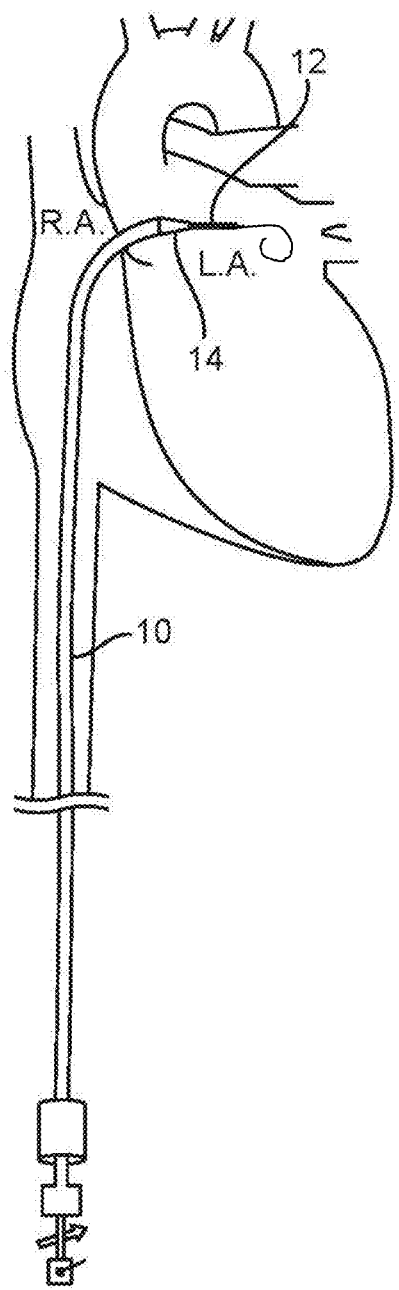
FIGS. 4A-4B illustrate transeptal passage of an RLC to the left atrium. More particularly, FIG. 4A schematically illustrates a section of the heart and shows the step of transeptal catheterization from the right atrium into the left atrium, using a Brockenbrough needle assembly through the RLC.
Figure 4B:
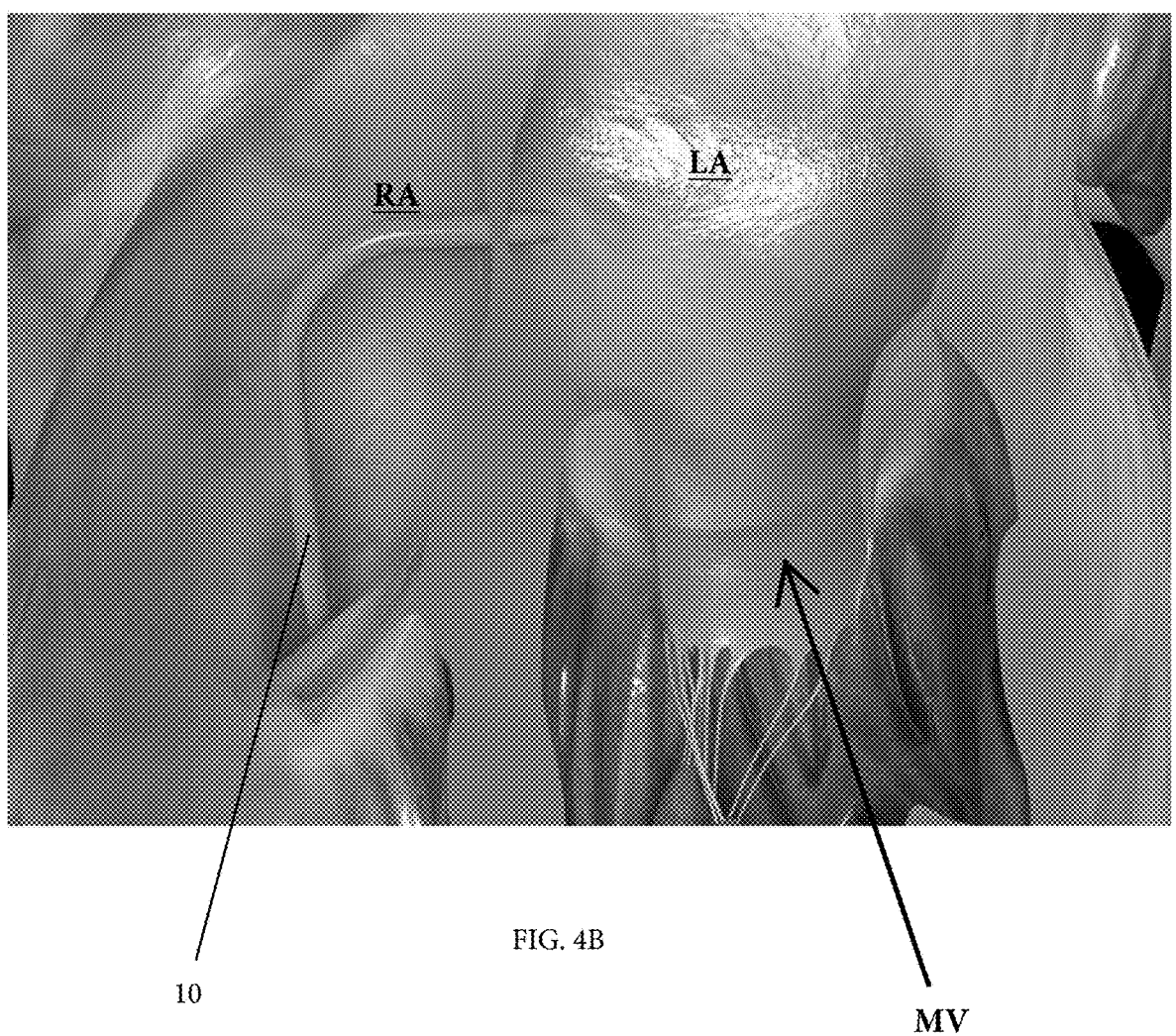
Figure 5:
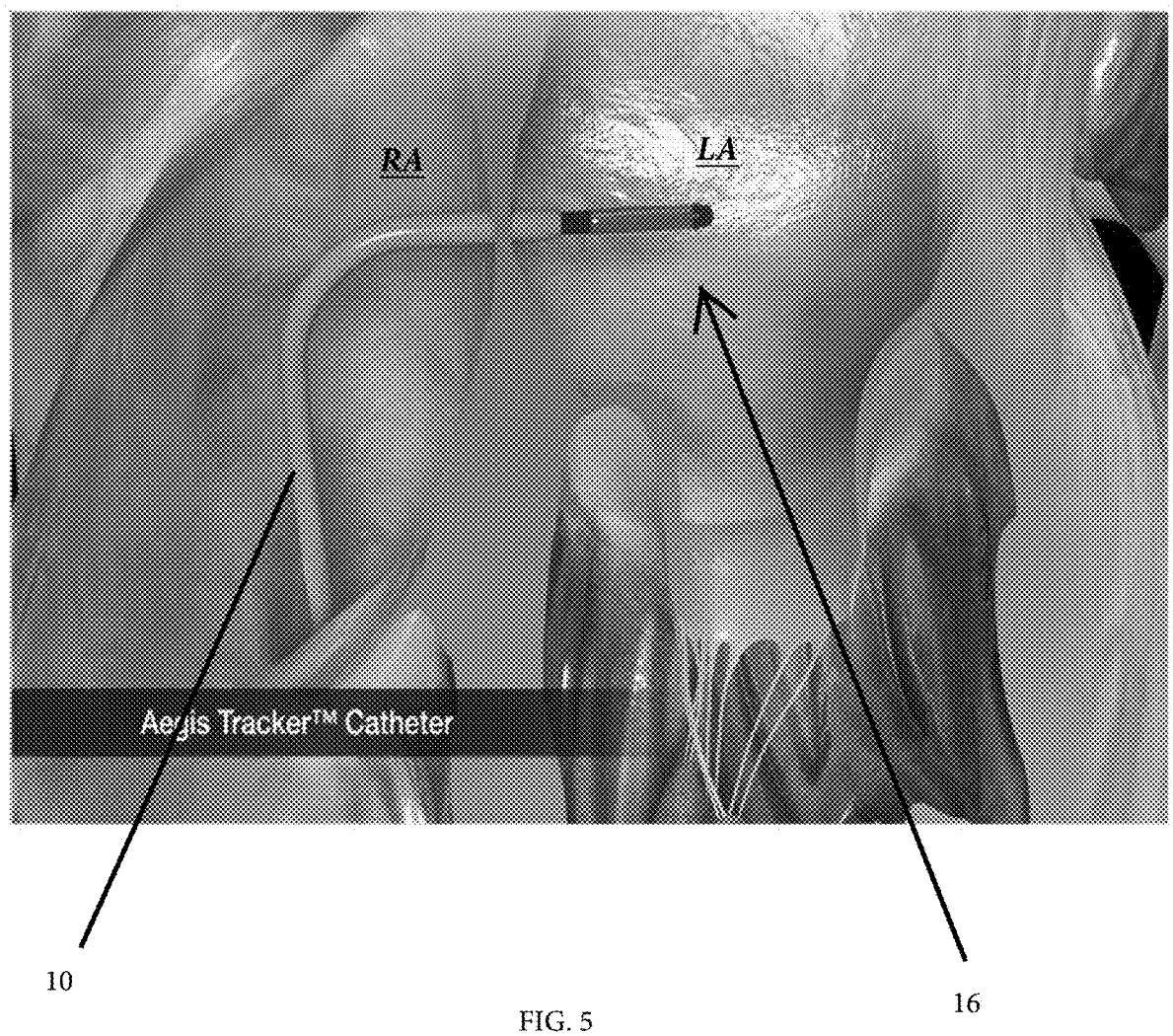
FIG. 5 shows introduction of the tracker balloon into the left atrium.
Figure 6:
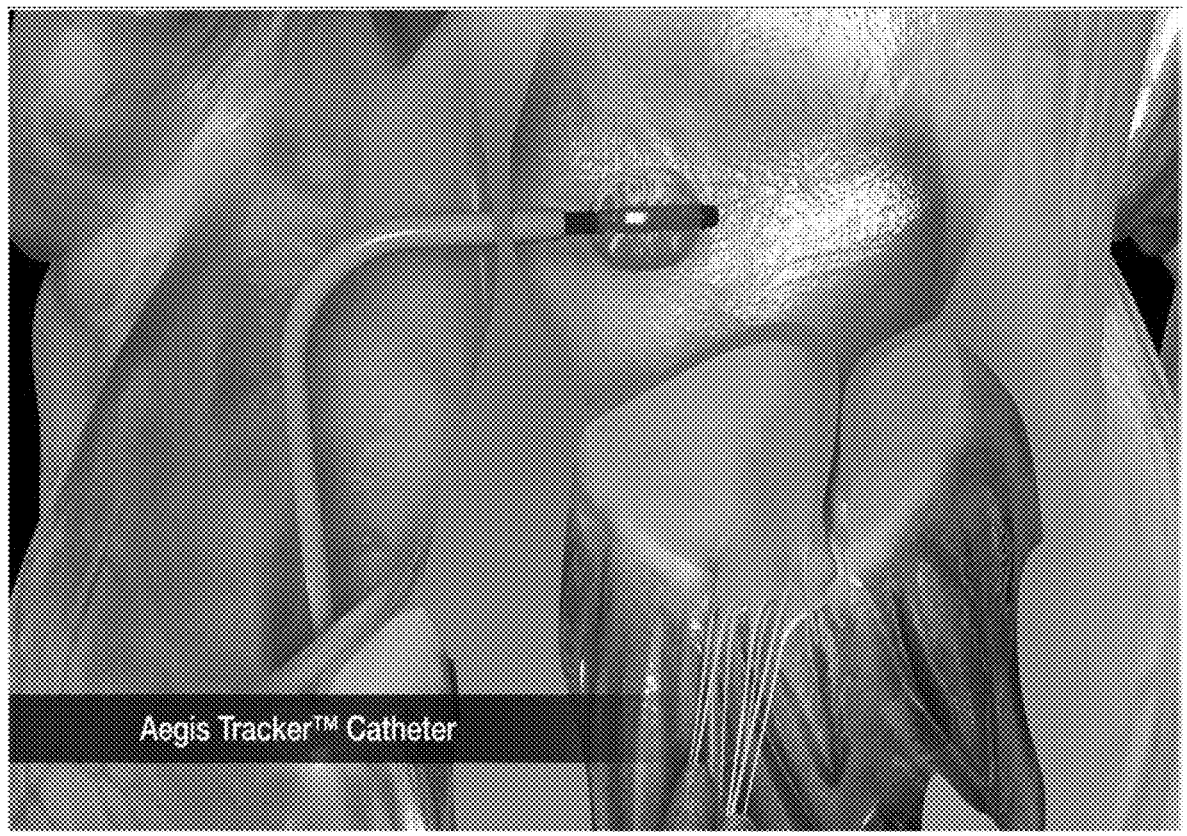
FIG. 6 shows inflation of the tracker balloon.
Figure 7:
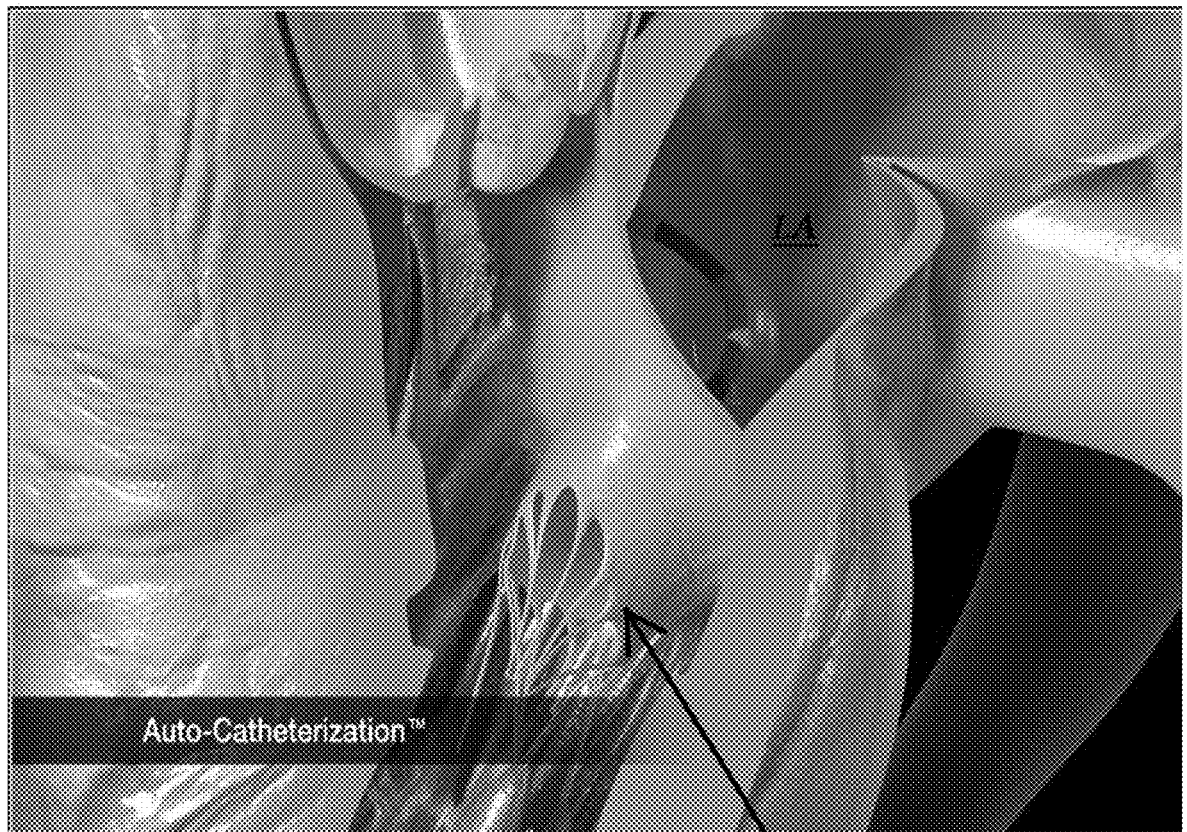
Figure 8:
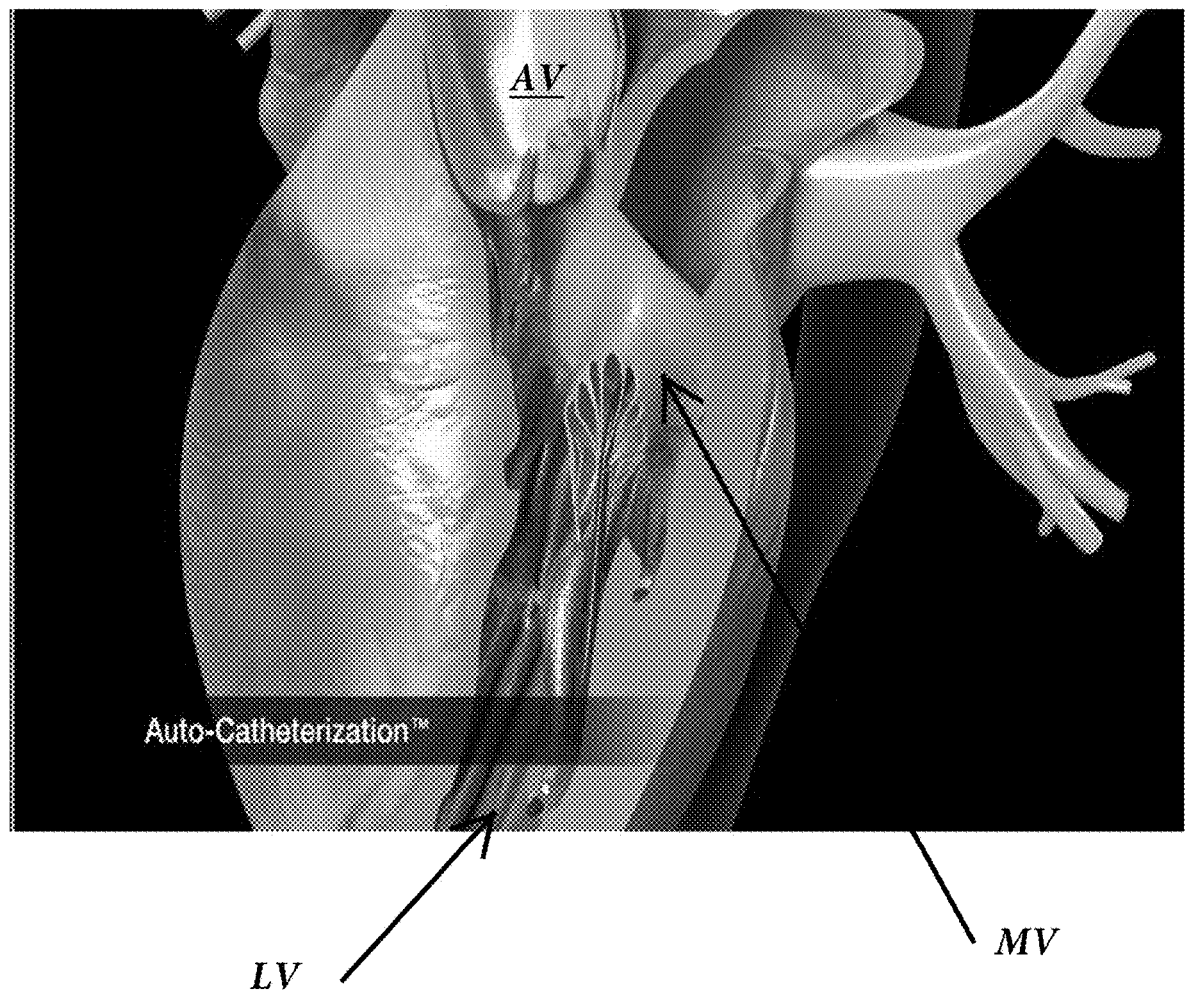
Figure 9:
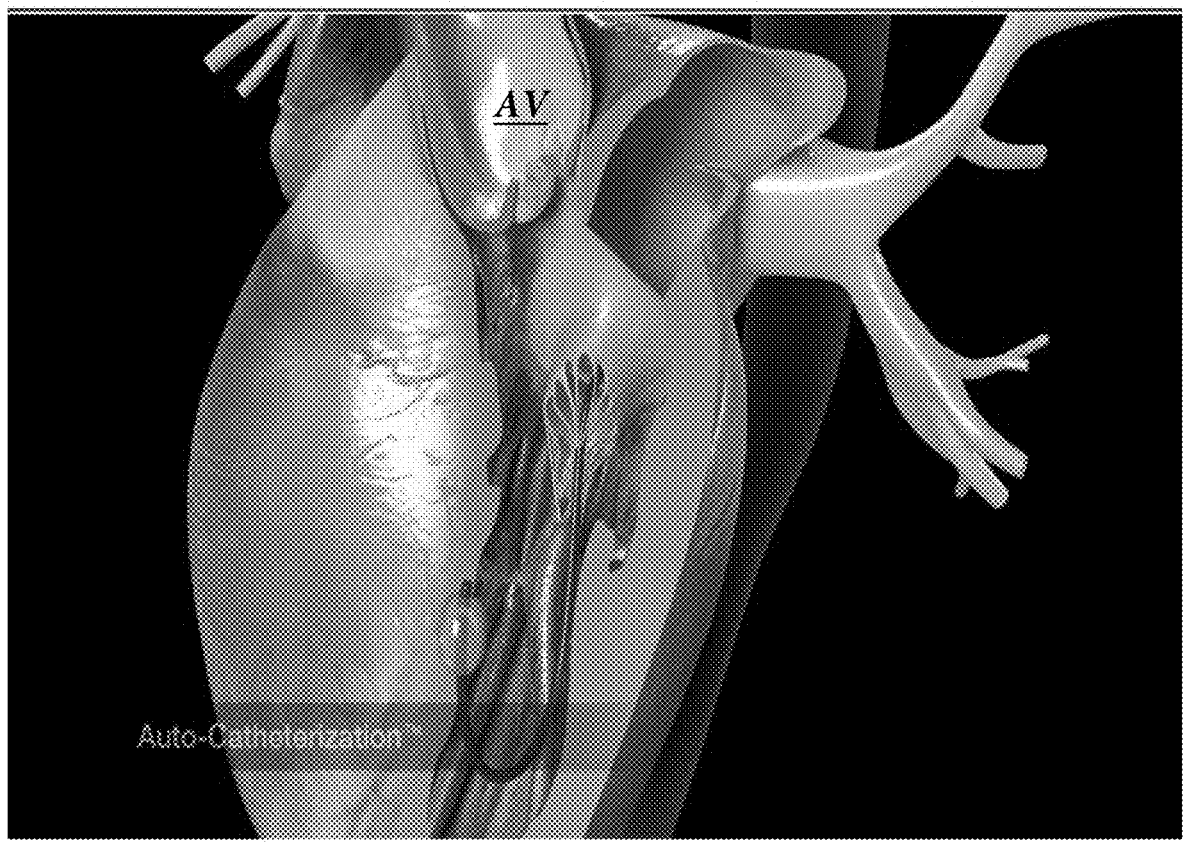
Figure 10:
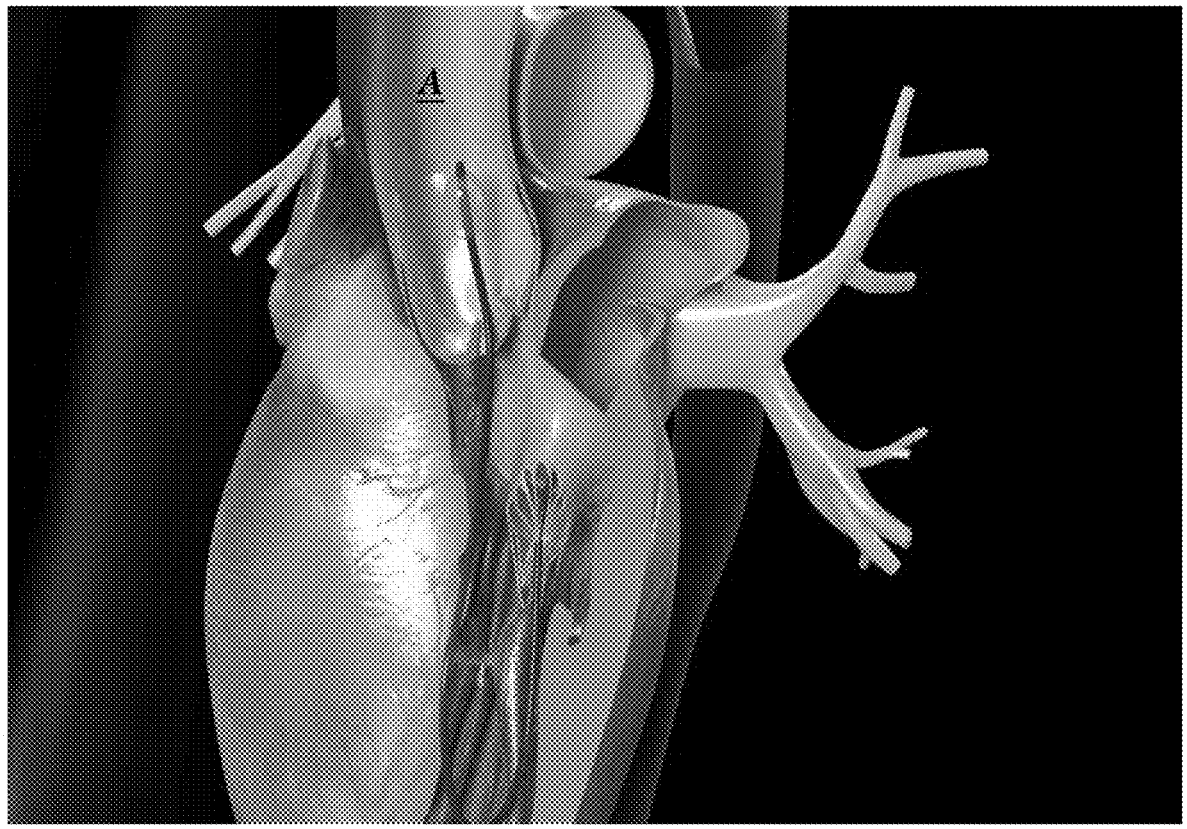
Figure 11:
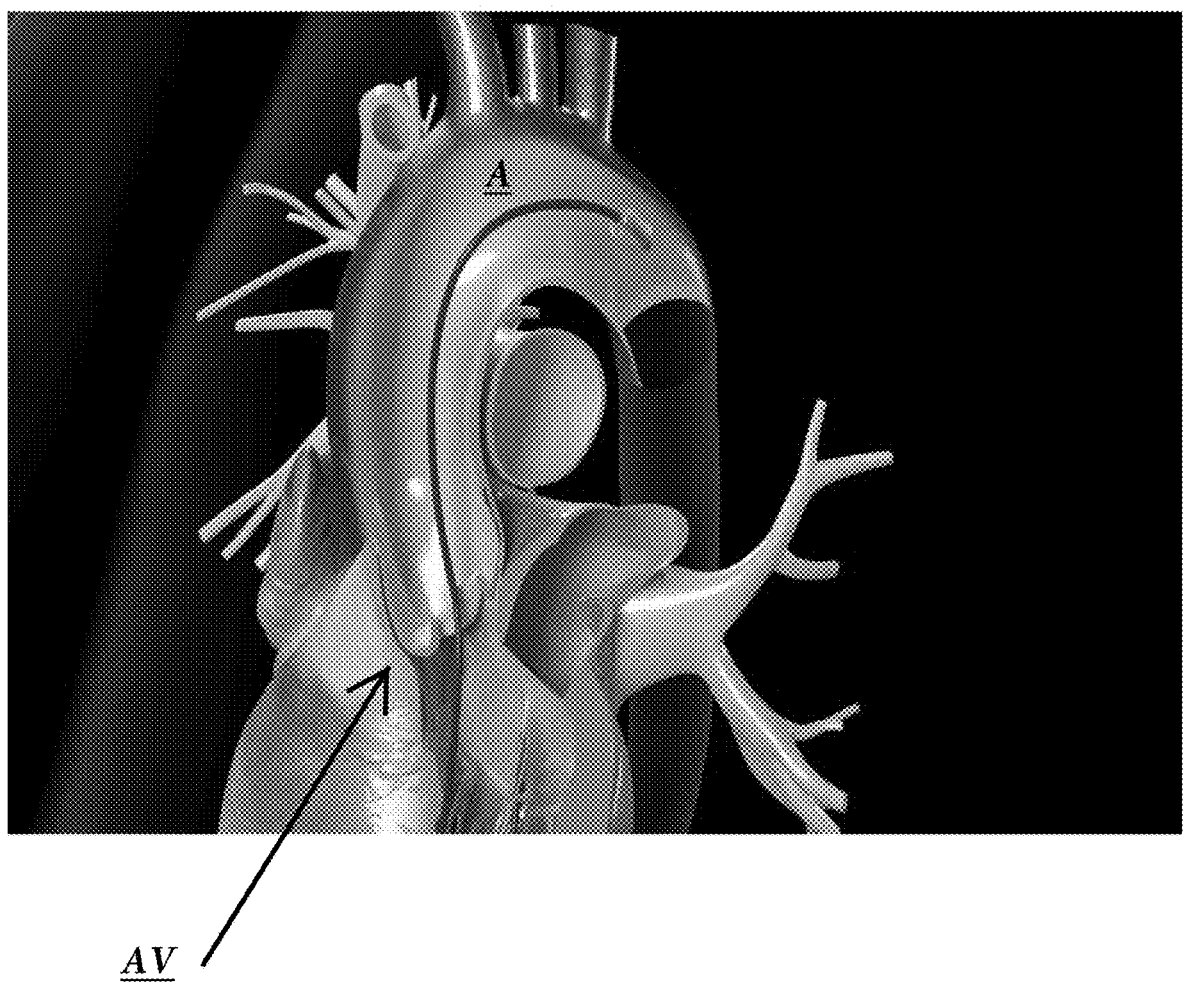
Figure 14:

As an initial step, the Right-Left Catheter (RLC) 10 is introduced using the well-known technique of transeptal catheterization from the right atrium (RA) into the left atrium (LA), such as by using a Brockenbrough needle assembly 12 through the RLC, which is positioned in the right femoral vein (RFV) as shown in FIG. 1. Once the distal end of the RLC is disposed in the left atrium (FIG. 4B), the needle is withdrawn and the tracker balloon catheter 16 is passed through the RLC into the left atrium. See FIGS. 5 and 6. The balloon may have a concave proximal face to increase the surface area of the balloon in the upstream direction. Once deployed within the left atrium, the flow of blood carries the tracker balloon into and through the mitral valve (MV) (FIG. 7), left ventricle (LV) (FIGS. 8 and 9), aortic valve (AV) and aorta (A) FIGS. 10 and 11 to the femoral artery (FIG. 12). This description describes left side access to the arterial vasculature, but in alternative methods the tracker balloon catheter may be diverted to the right femoral artery (RFA). The RLC is then advanced over the tracker balloon catheter towards the left or right femoral artery. FIGS. 13 and 14.

Figure 15:
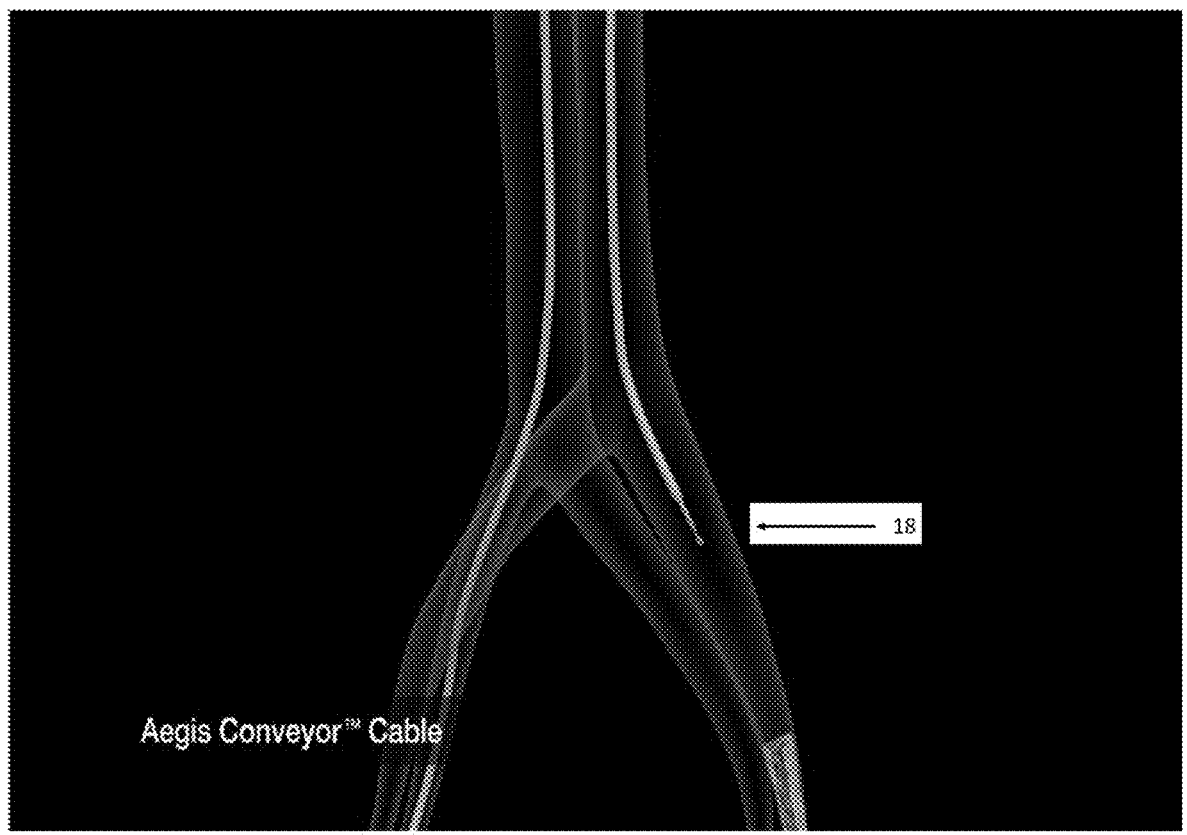
FIG. 15 shows the cable advanced through the RLC with its ball tip exposed from the end of the RLC.
Figure 16:
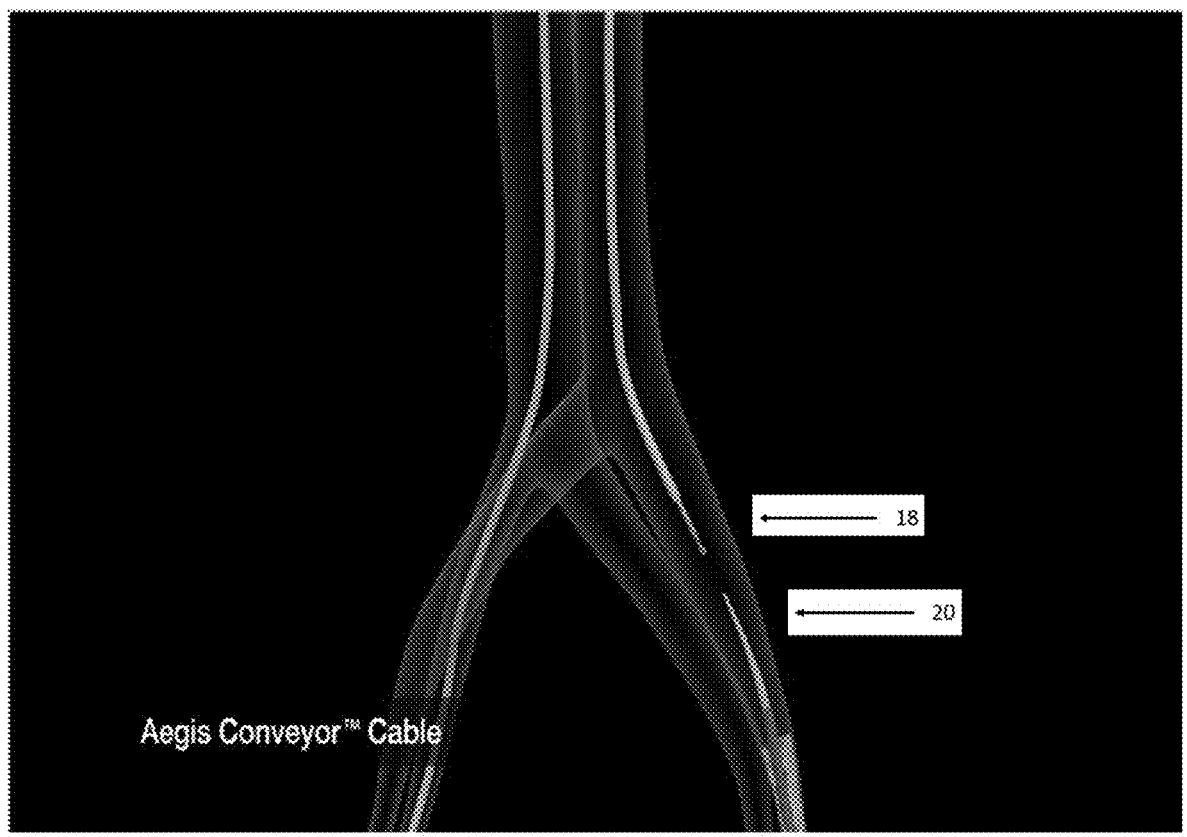
FIGS. 16-21B illustrate snaring of the ball tip of the cable in the left femoral artery after the cable been passed through the RLC.
Figure 17:
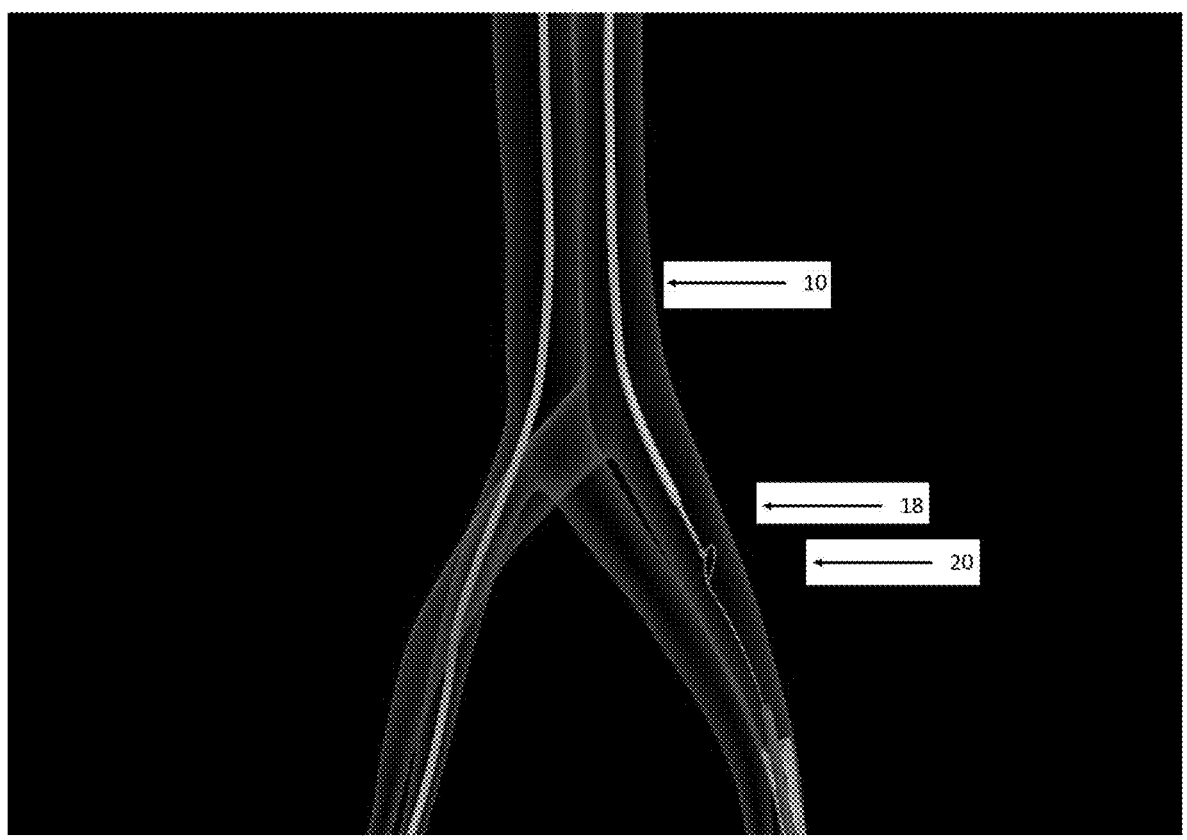
Figure 18:
Figure 19:
Figure 20:

The tracker balloon catheter 16 is deflated (FIG. 14) and then withdrawn from the RLC 10, and the conveyor cable 18 is inserted into the RLC on the patient's right ride and advanced. This directs the tip of the cable into the left femoral artery. FIG. 15. A snare 20 introduced into the left femoral artery grasps the ball tip of the conveyor cable as shown in FIGS. 16-19, and withdraws the ball tip out the femoral artery (FIG. 20).

Figure 21A:
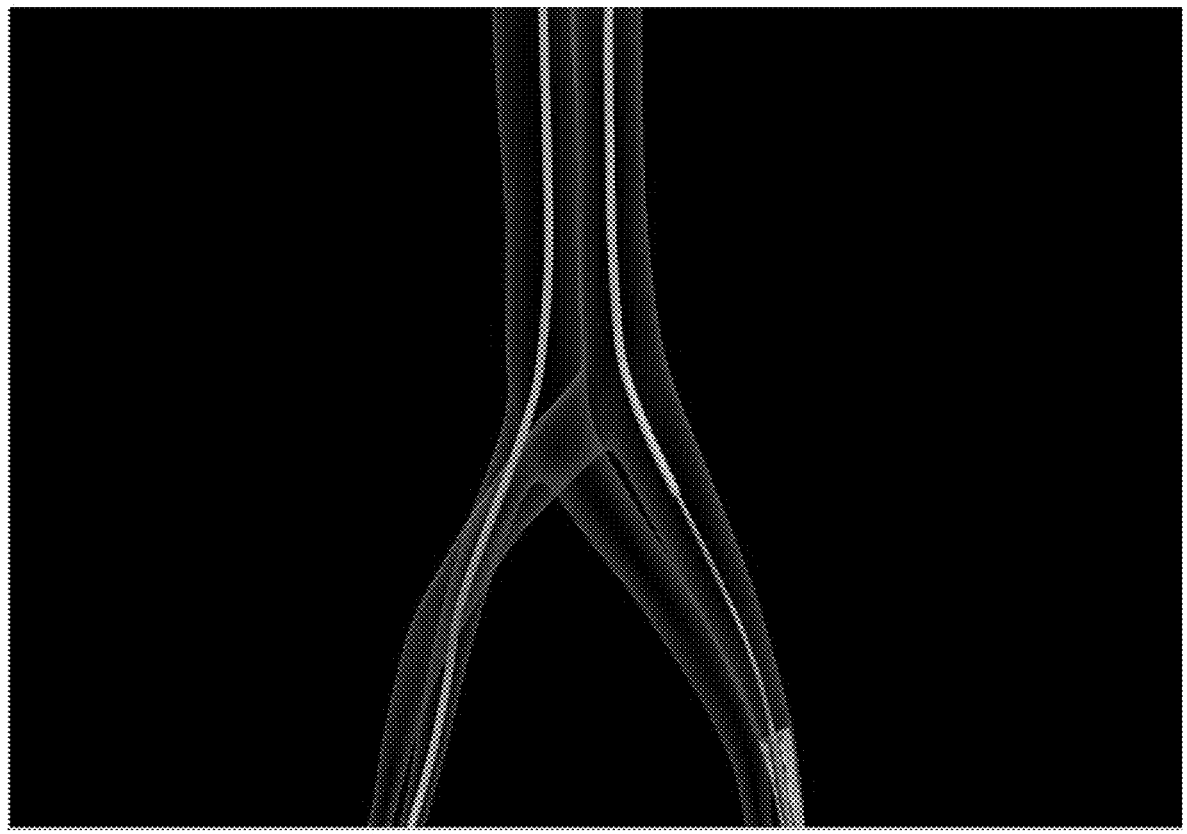
Figure 21B:
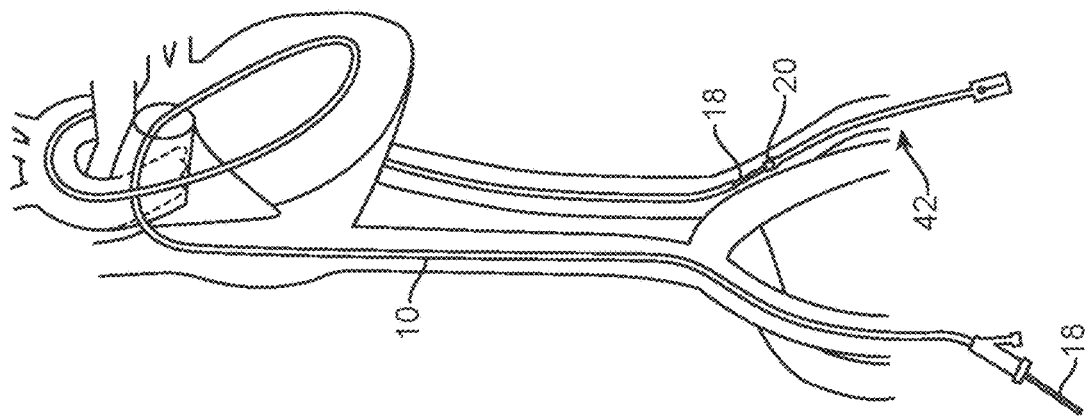

The left ventricle redirector (LVR) is introduced over the cable (FIG. 21). The lumen of the LVR slides over the ball tip and shaft of the cable. The LVR is pushed towards the RLC while the RLC is pushed towards the LVR, causing the LVR to advance its distal end over the exterior surface of the RLC. This eliminates the exposed section of cable between the LVR and RLC, and because the conveyor cable is much more flexible than the LVR or RLC, this step removes flexibility from the assembly now extending through the vasculature and heart.

Figure 23:
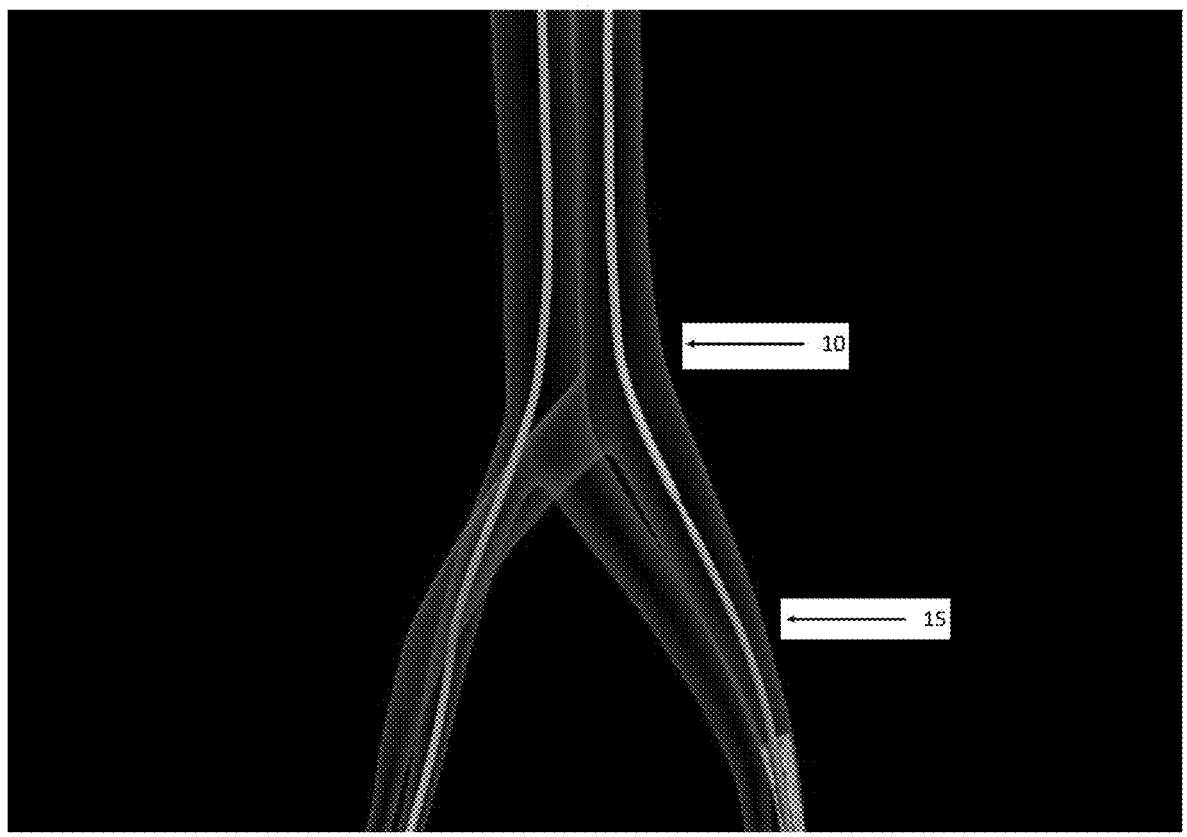
FIGS. 23-25B also illustrate the steps of advancing the LVR over the cable and the advancement of the LVR. Note that as shown in these drawings, a tapered dilator may be used in this step in advance of the LVR.
Figure 24:
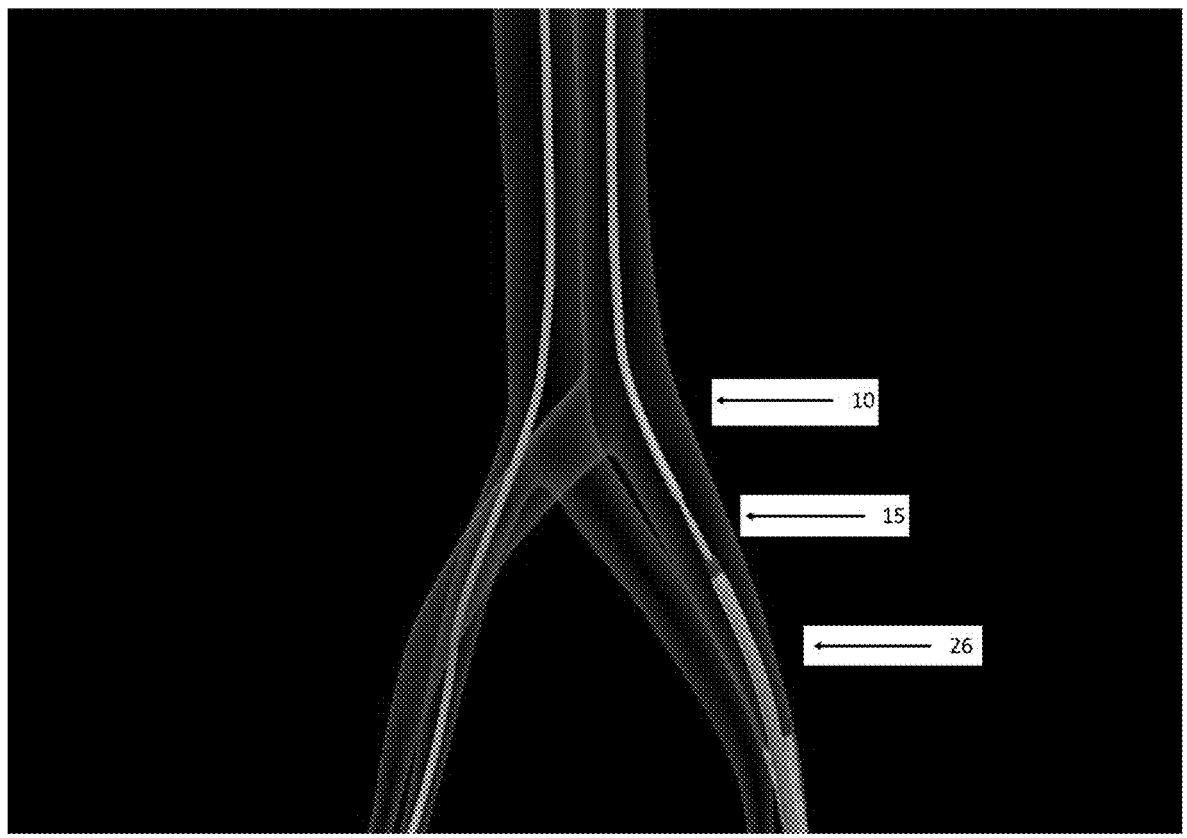

Alternatively, as shown in FIGS. 23-24, a tapered dilator 15 may be used in this step in advance of the LVR. As shown in FIG. 23, the dilator may be advanced over the cable and have its tapered tip inserted into the RLC. Then, as shown in FIG. 24, the LVR may be advanced over the dilator to the RLC.

Figure 22B:
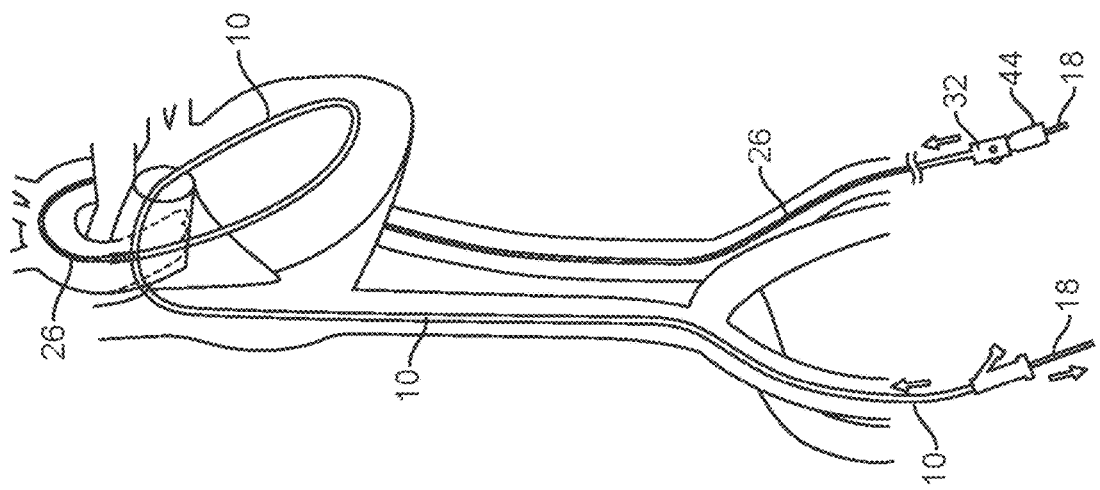
FIG. 22B illustrates the advancement of the LVR.
Figure 22A:
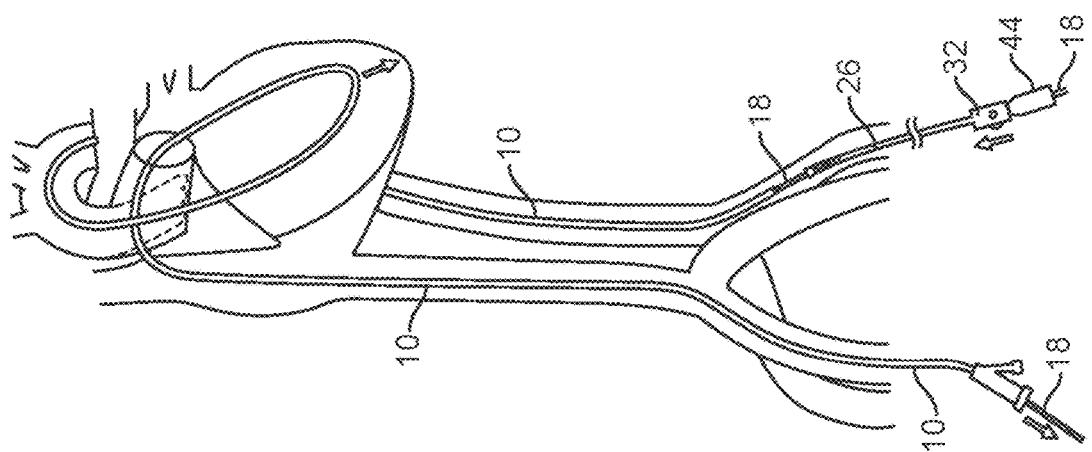
FIG. 22A illustrates the step of advancing the LVR over the cable and the locking of the LVR to the cable.
Figure 25A:
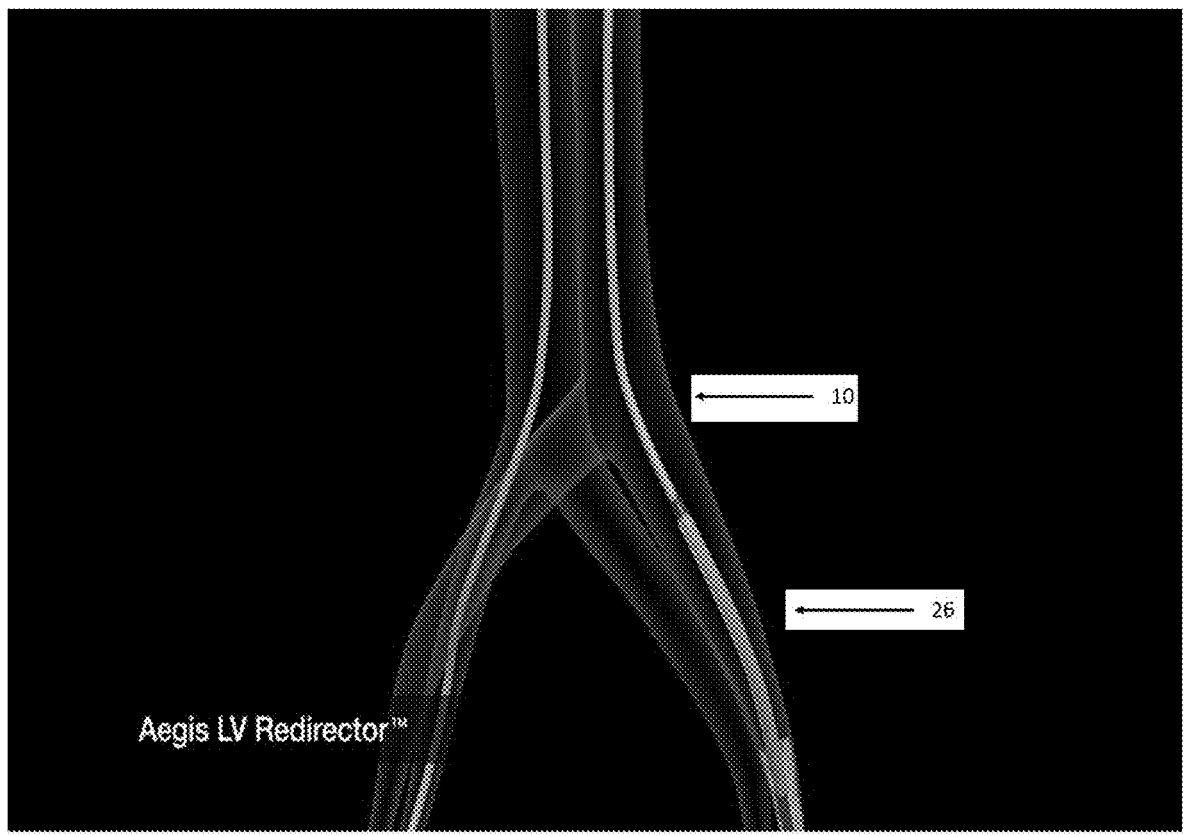
Figure 25B:
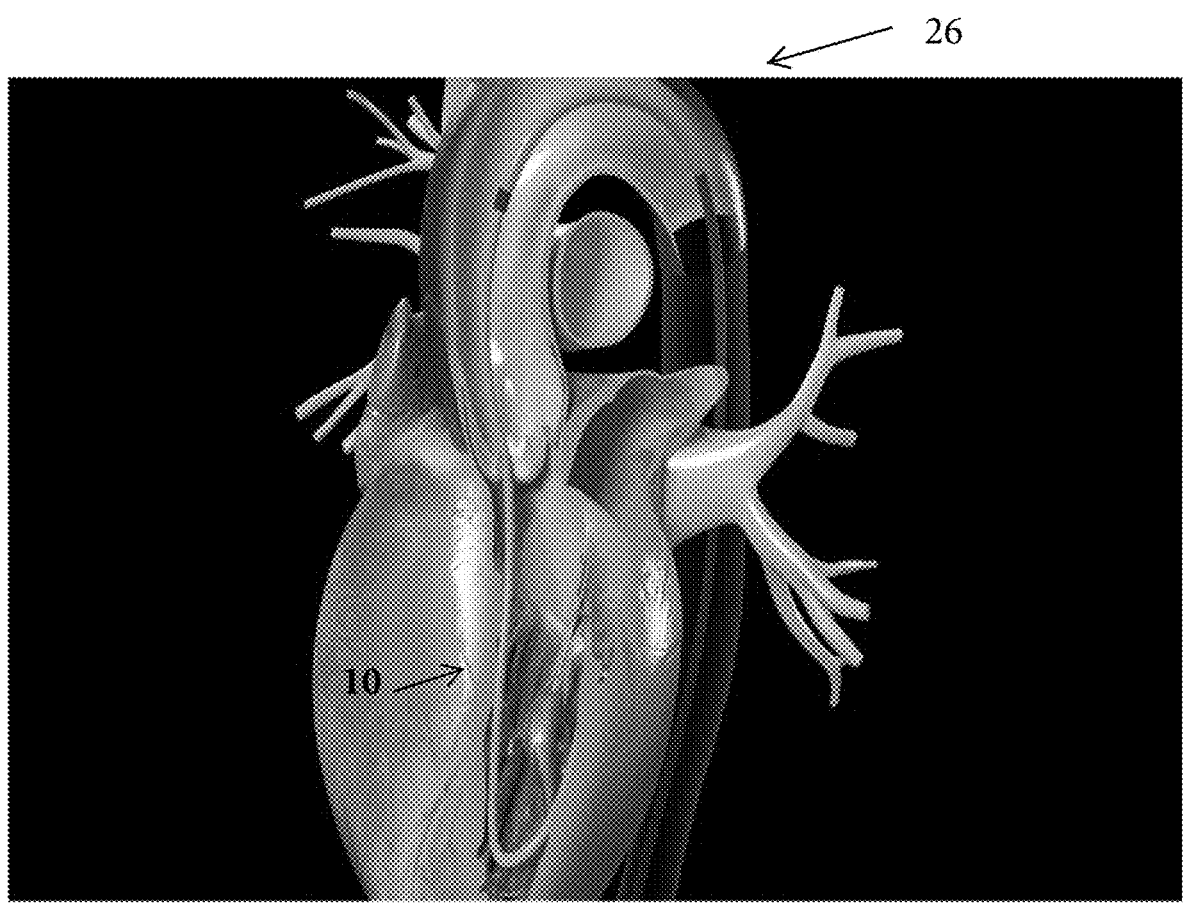

A cable lock may be used to lock the proximal end of the LVR onto the conveyor cable outside the access point to the femoral artery so that the LVR and cable will move together. The user pulls on the cable on the patient's venous side (the patient's right which is the left side of the drawings). On the patient's arterial side (the right side of the drawings), the user pushes the LVR. FIG. 22B. Note that since the LVR is locked to the conveyor cable, the actions of pulling the cable and pushing the LVR advance the LVR into the aorta. FIGS. 22B, 25A and 25B. If the system is configured such that the LVR slides over the RLC or remains engaged with the RLC by the dilator or other means, this step is accompanied by the pushing on the RLC from the venous side. Pushing the RLC during advancement of the LVR pushes the loop of the LVR into the apex of the LV, keeping it away from delicate valve structures and chordae tendineae.

Figure 26:
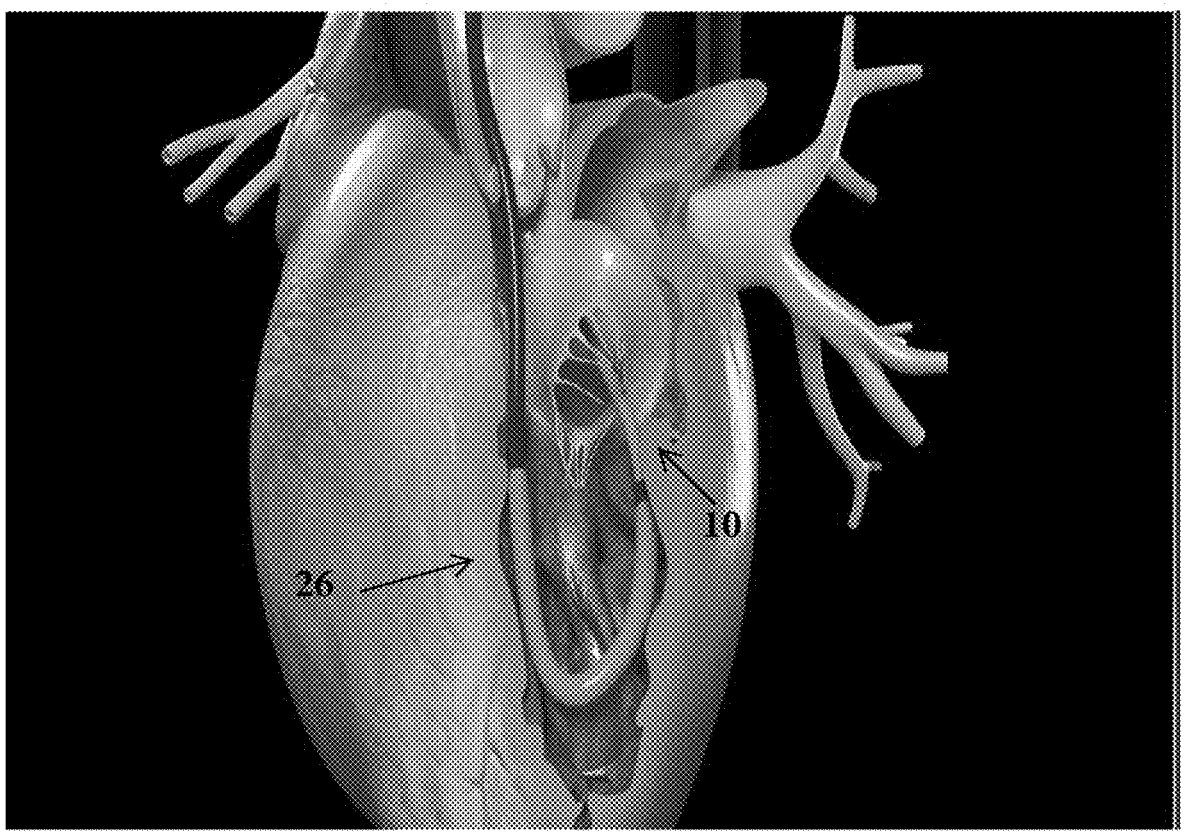
FIG. 26 shows the LVR moved into the left ventricle.
Figure 27:
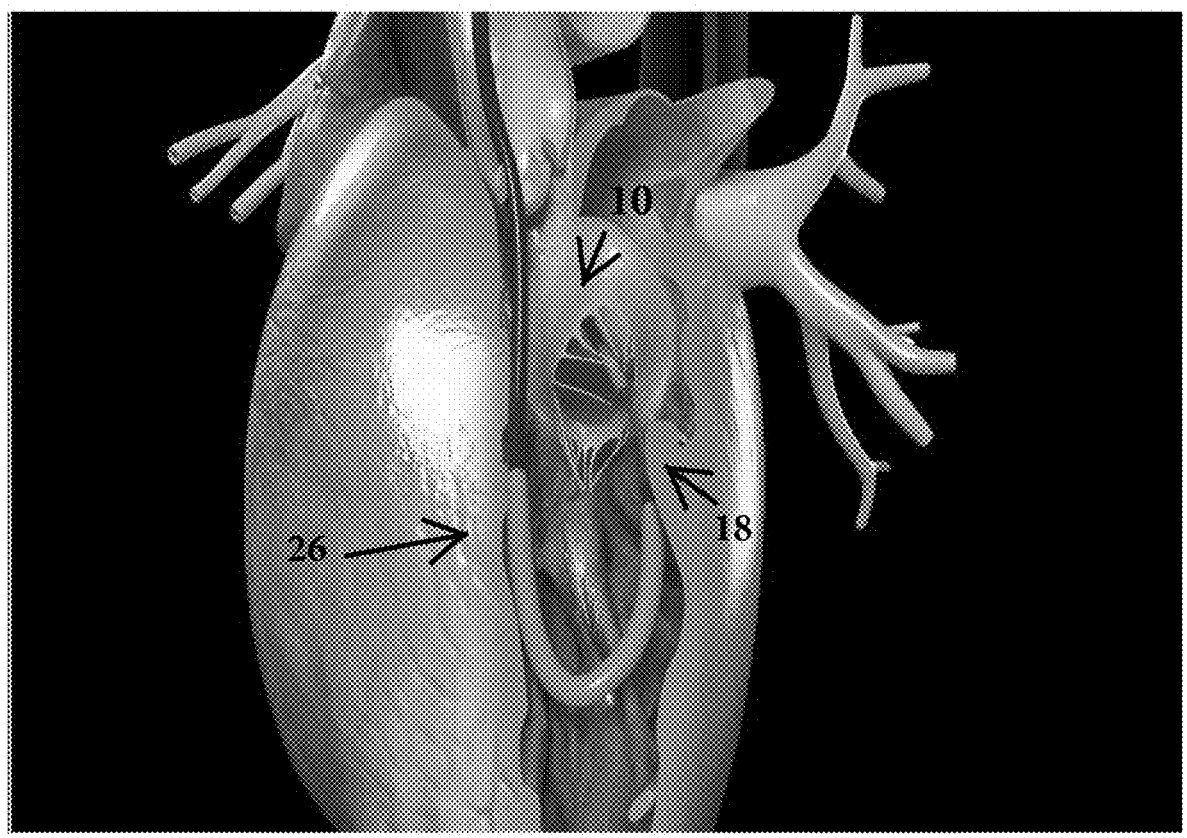
FIG. 27 is similar to FIG. 26 and also shows the RLC beginning to be removed.

Once within the heart, the LVR is pushed strongly into the apex of the left ventricle by a pushing force applied to its proximal end. FIG. 26.

Figure 28A:
Figure 28B:
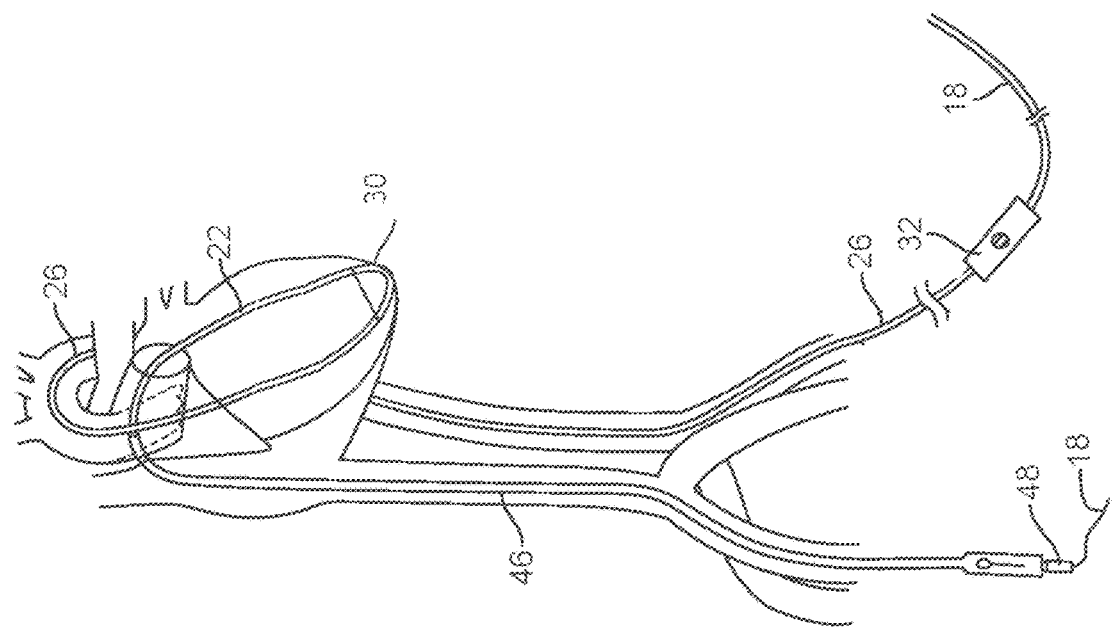

The RLC is next withdrawn from the venous side. The cable is still in place as shown. The AVTD is connected to the cable. FIG. 28. A segmental tensioner and cable lock may be used in the manner described in PCT/US17/62913.

Figure 29A:
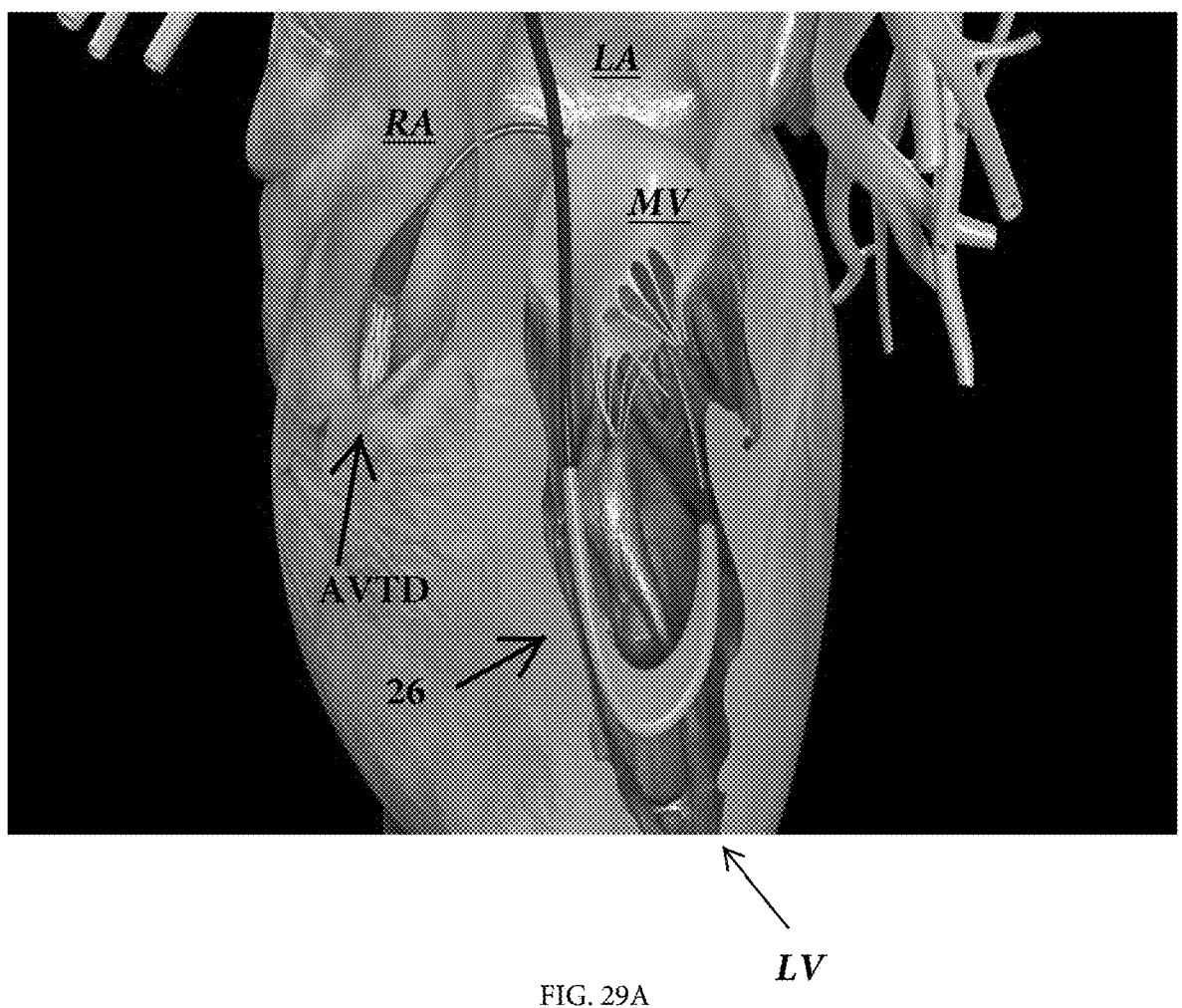
Figure 29B:
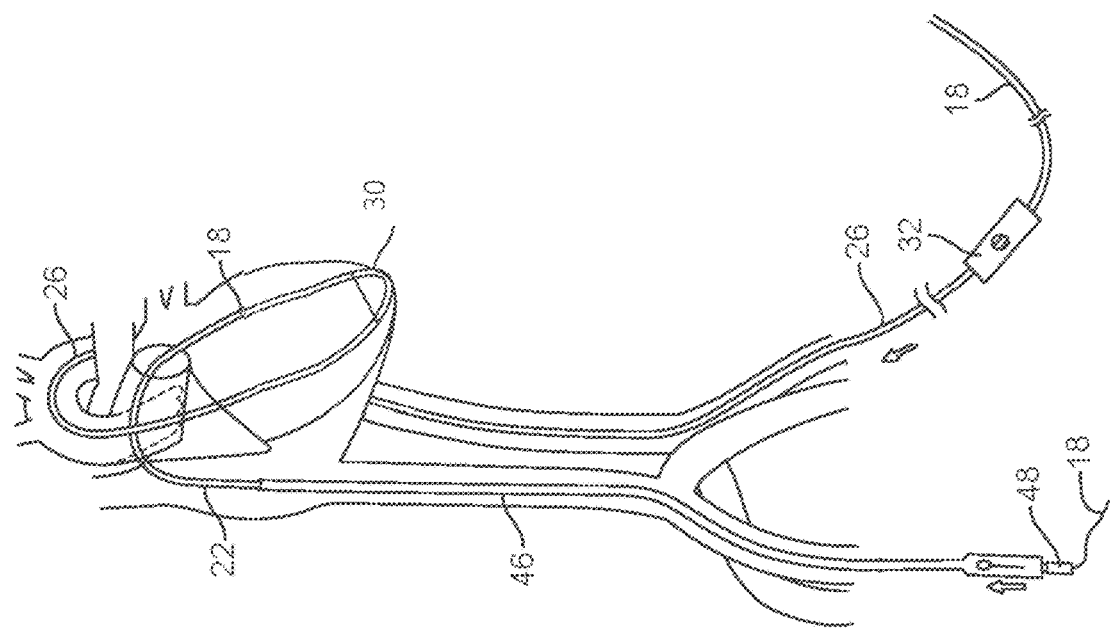
Figure 29C:
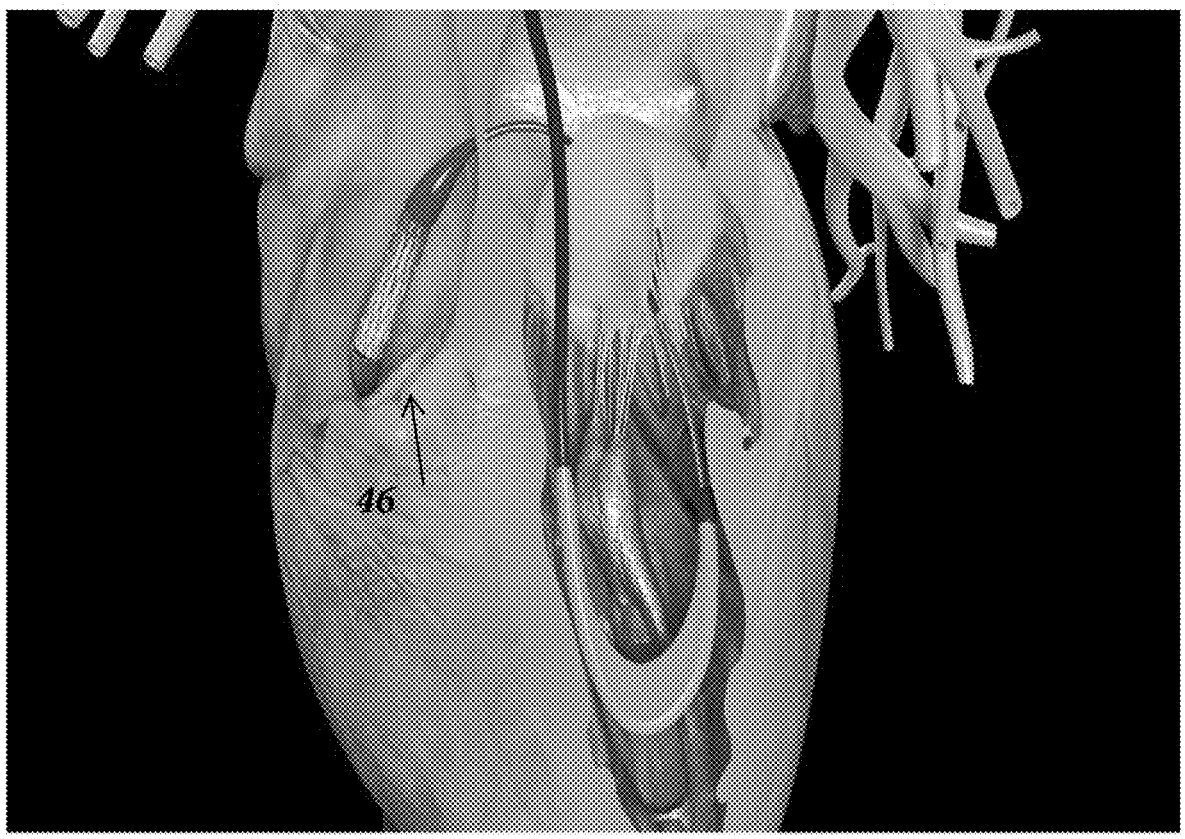
Figure 30:
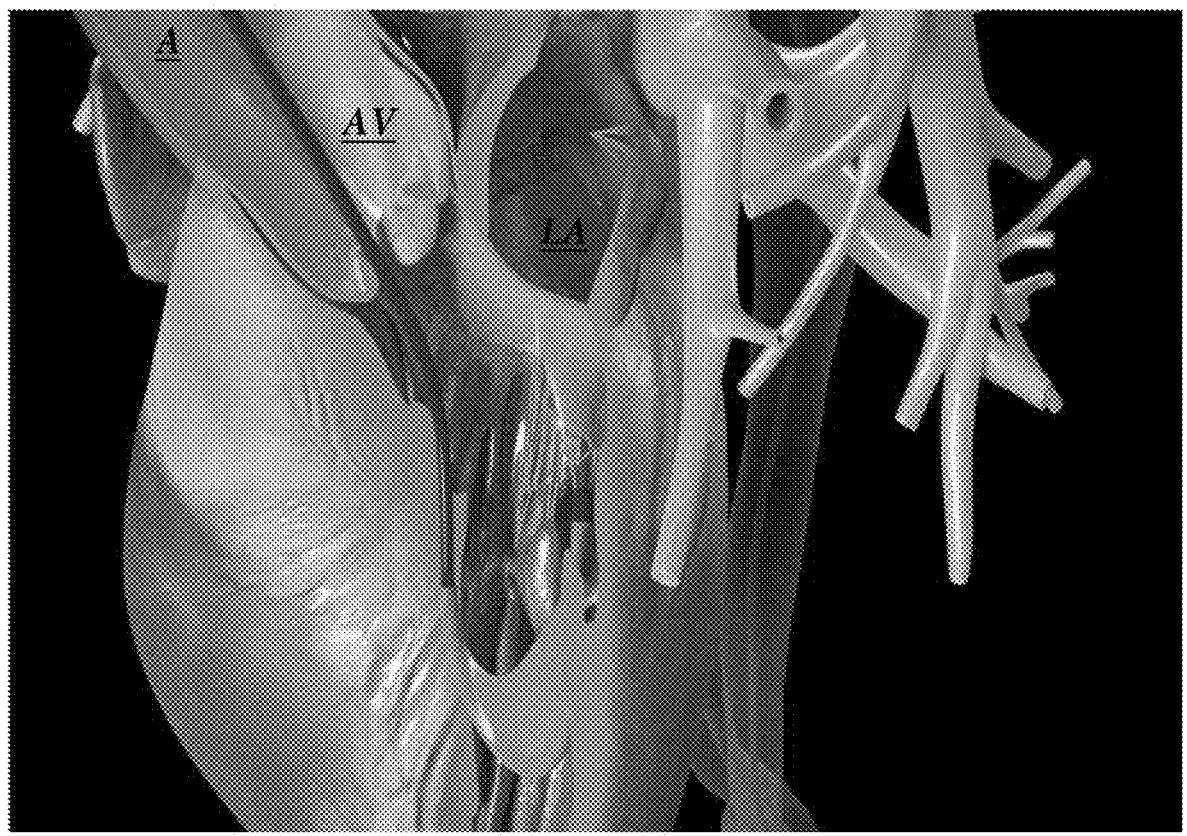
FIGS. 30 and 31 show the TAVR system being advanced across the septum into the left atrium towards the mitral valve ring.
Figure 31:

Once the AVTD has entered the venous circulation it is advanced toward the right atrium (FIGS. 29A and 29B), (optionally led by the segmental tensioner 22), as the system is pulled by the cable while the AVTD is simultaneously pushed along at the same rate in a coordinated manner. The optional segmental tensioner leads the way as it crosses the interatrial septum (FIG. 30) and provides a gradual transition to the bigger and stiffer AVTD.

Figure 32:
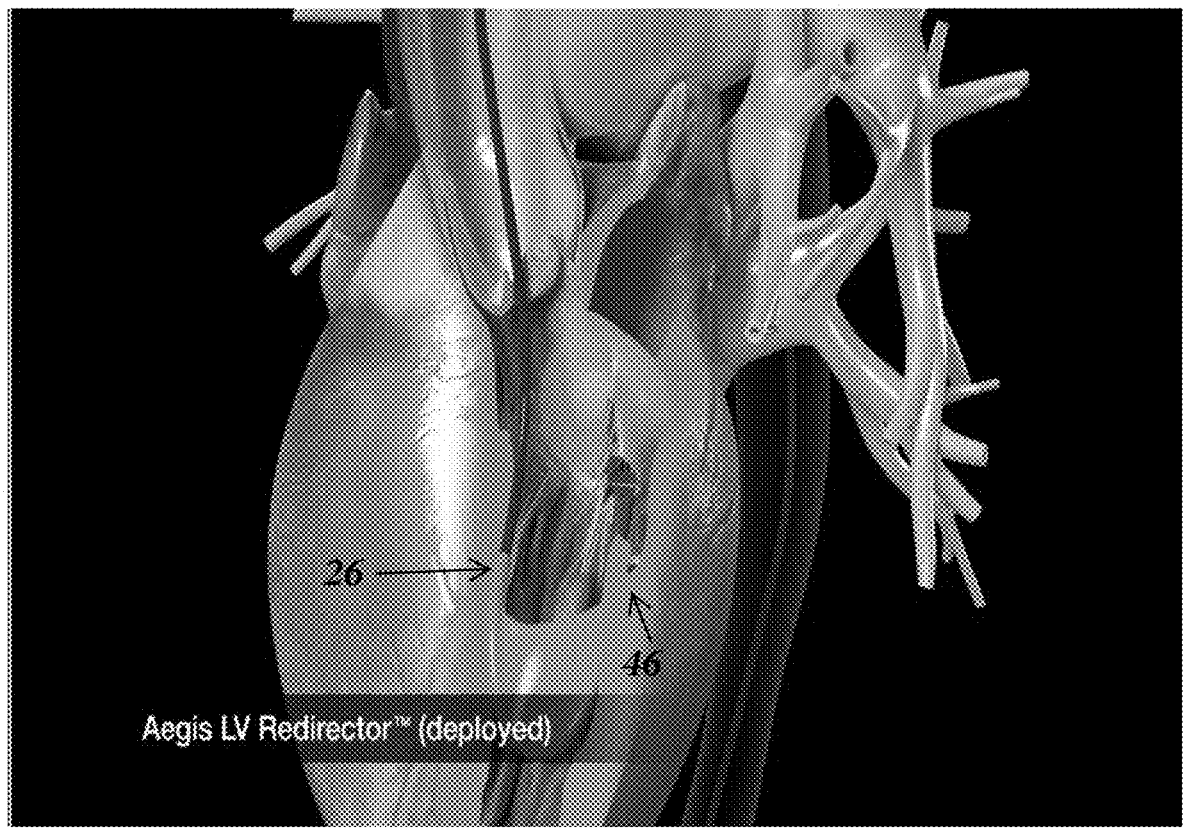
FIG. 32 shows the LVR in the left ventricle as the TAVR system is advanced into contact with the LVR. Note that the LVR may be provided without the membrane of the LVR.

At this point, a significant pulling force is applied to the AVTD/tensioner assembly by the cable. This force is slightly more than the "push force" force on the AVTD so as to pull the distal nose of the AVTD down and to the patient's left through the interatrial septum. FIG. 32. Despite the pushing force of the LVR into the apex, with ever increasing pull force, there is a strong tendency to cause the loop of the cable contained in the steerable section of the LVR to be pulled upward into the valve structures above. This tendency is overcome by the synergistic downward pushing force exerted by the segmental tensioner as it enters the lumen at the distal end of the LVR in the LV apex. It ensures that the cable is positioned away from the aortic and mitral valve leaflets and chordae tendineae by maintaining the cable safely away from the valve structures within the LVR's protective sleeve.

Figure 33:
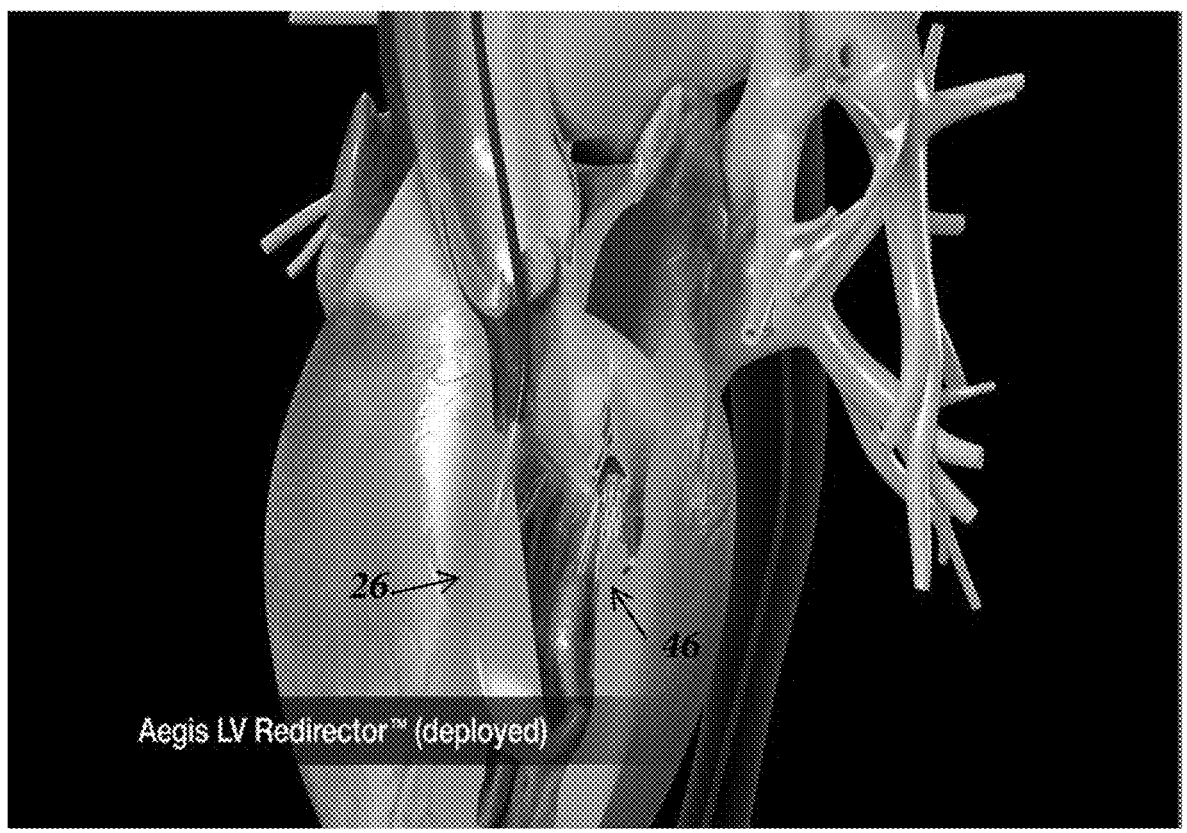
FIG. 33 shows the LVR deployed and further shows the TAVR delivery system, which is in contact with the LVR, positioned at the mitral valve as the TAVR delivery system is being centered within the valve.
Figure 34:
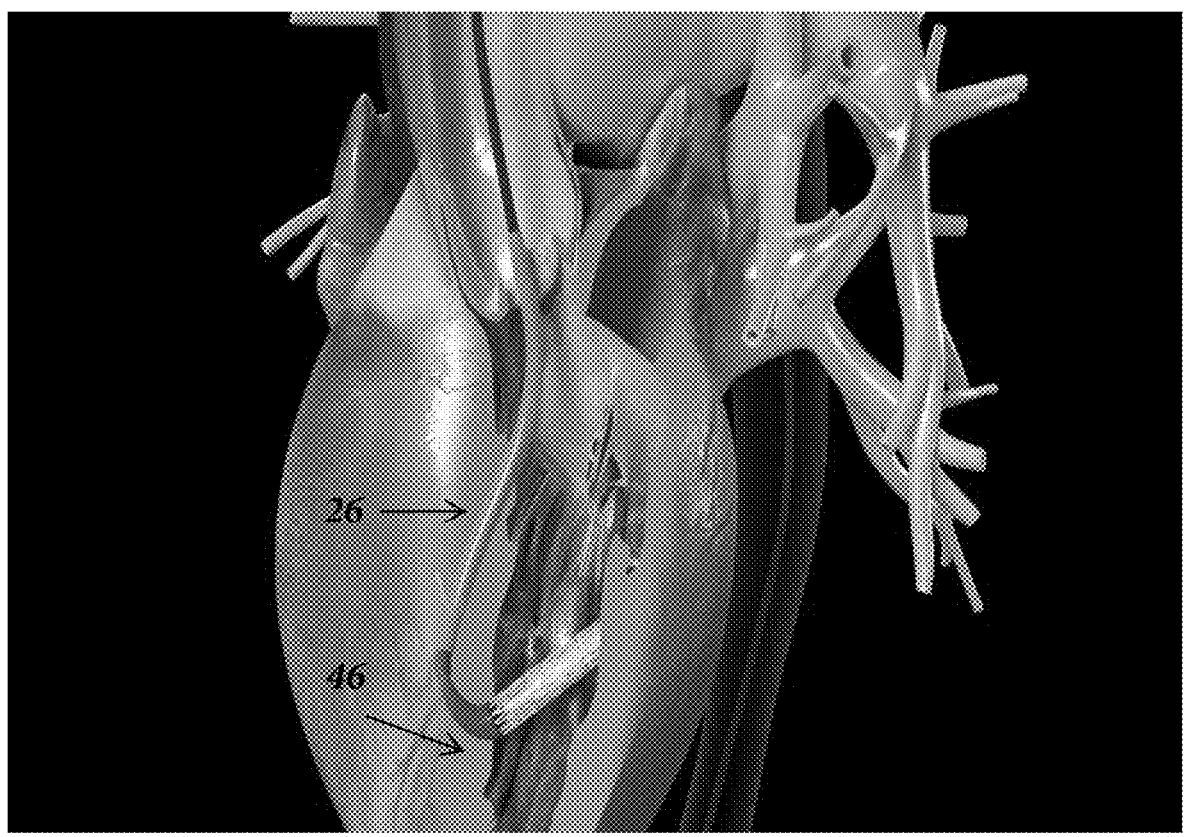
FIG. 34 shows the TAVR delivery system in the left ventricle moving towards the aortic valve, the LVR has been moved out of the deployed position and is passing through the aortic valve while remaining in contact with the LVR.
Figure 35:
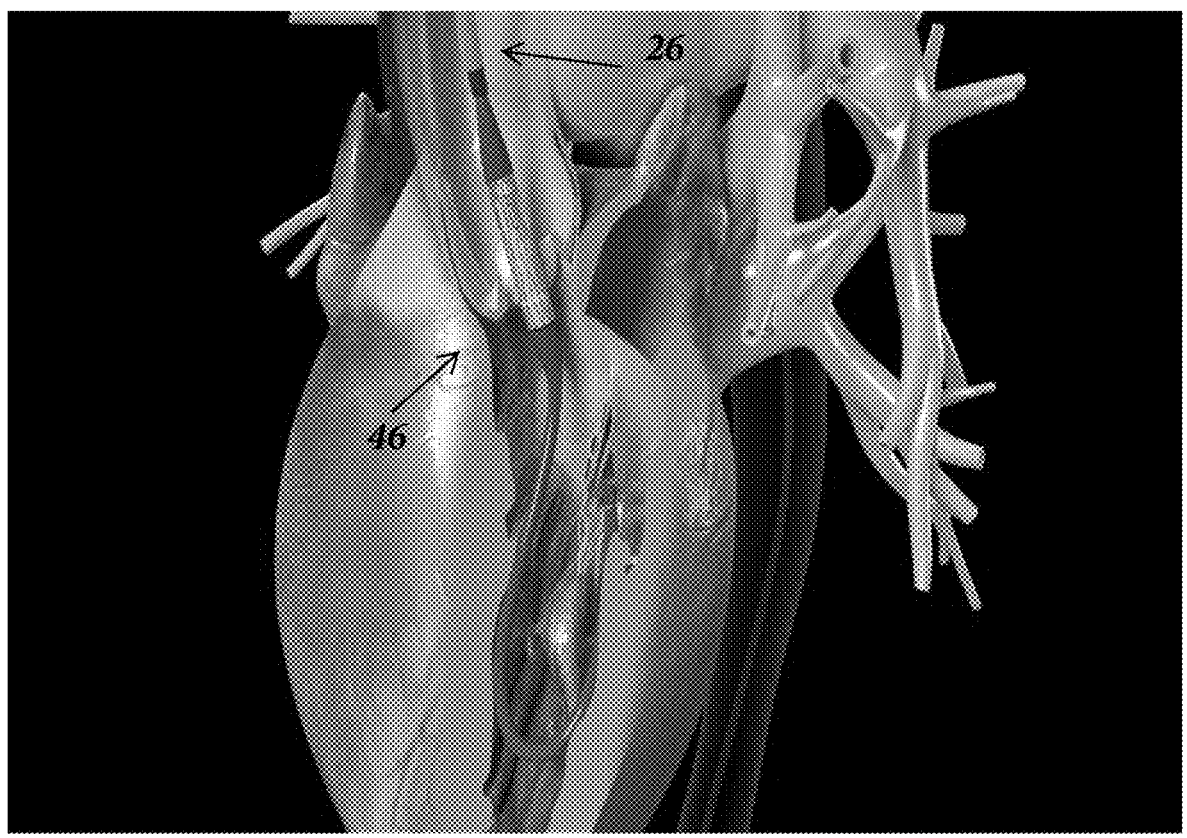
FIG. 35 shows the TAVR device advanced through the aortic valve site while remaining in contact with the open end of the LVR.

The pullwire of the LVR is activated, placing its protective panel in the deployed position in the left ventricle. FIG. 33. In addition to the importance of maintaining the cable loop in the apex of the ventricle, another key function of the LVR is to aid in the steering of the AVTD through the center of the mitral valve ring at an angle that is perpendicular to the mitral valve ring plane. Once through the mitral valve (FIGS. 33 and 34) and into the left ventricle, the AVTD is further advanced to the aortic valve location as shown in FIG. 35.

All patents and patent applications referred to herein, including for purposes of priority, are fully incorporated herein by reference.

We claim:

1. A method of delivering an aortic valve therapeutic device to an aortic valve site, comprising the steps of:
   (a) percutaneously introducing a cable into a vasculature of a patient and positioning the cable to run from a femoral vein, through a heart via a transeptal puncture, and to a femoral artery, the positioned cable having a first end external to the patient at the femoral vein and a second end external to the patient at the femoral artery;
   (b) securing an aortic valve therapeutic device to the first end of the cable;
   (c) pushing the aortic valve therapeutic device from the femoral vein while pulling the second end of the cable from the femoral artery to advance the aortic valve therapeutic device to the aortic valve site;
   (d) providing a left ventricle redirector (LVR) having a tubular lumen, a distal end actively steerable to form a curve;
   passing the distal end of the lumen of the LVR over the second end of the cable at the femoral artery and advancing the LVR though an aorta and aortic valve to a left ventricle, actively forming a curve in the distal end of the LVR;
   engaging a distal nose of the aortic valve therapeutic device with the distal end of the LVR;
   seating an edge of the curve of the LVR within an apex of the left ventricle; and
   during step (c), applying a force to the LVR from the femoral artery to press the curve into the apex of the left ventricle.

2. The method of claim 1, wherein applying the force to the LVR orients the distal nose of the aortic valve therapeutic device inferiorly and towards the patient's left.

3. The method of claim 1, wherein applying the force to the LVR prevents migration of the LVR into valve leaflets of a mitral valve.

4. The method of claim 1, wherein engaging the distal nose of the aortic valve therapeutic device with the distal end of the LVR includes:
   providing a tubular connector having a distal end and a proximal end;
   inserting the distal nose of the aortic valve therapeutic device into the proximal end of the tubular connector;

causing the distal end of the tubular connector to pass into the distal end of the LVR.

5. The method of claim 4, further including the step of steering the aortic valve therapeutic device through a mitral valve ring using any combination of torqueing the LVR, advancing or retracting the LVR in a proximal or distal direction, or actively modifying tension on a pullwire used to actively steer the curve of the LVR.

6. The method of claim 1, wherein the method includes introducing a right-to-left conduit (RLC) from the femoral vein into an inferior vena cava into a right atrium, through an interatrial septum into a left atrium, through a mitral valve to the left ventricle, and through the aortic valve into the aorta, and wherein step (a) includes introducing the second end of the cable into the RLC at the femoral vein.

7. The method of claim 6, wherein:
the method includes:
  positioning an expandable balloon of a balloon catheter in the right atrium and passing the balloon through the interatrial septum into the left atrium;
  inflating the balloon, causing the balloon catheter to be carried by blood flow through the aorta to the femoral artery;
  introducing the RLC over a proximal end of the balloon catheter;
  advancing the RLC over the balloon catheter to position a distal end of the RLC in the femoral artery; and
step (c) includes:
  advancing the second end of the cable to the distal end of the RLC; and
  capturing the second end of the cable via the femoral artery and positioning the second end external to the body.

8. The method of claim 7, wherein the step of capturing the second end includes advancing a snare into the vasculature via the left femoral artery and engaging the second end of the cable using the snare.

9. The method of claim 1, wherein the aortic valve therapeutic device is an aortic valve delivery system carrying a replacement aortic valve.

10. A method of delivering an aortic valve therapeutic device to an aortic valve site, comprising the steps of:
(a) percutaneously introducing a cable into a vasculature of a patient and positioning the cable to run from a femoral vein, through a heart via a transeptal puncture, and to a femoral artery, the positioned cable having a first end external to the patient at the femoral vein and a second end external to the patient at the femoral artery, wherein introducing the cable includes introducing a right-to-left conduit (RLC) from the femoral vein into an inferior vena cava into a right atrium, through an interatrial septum into a left atrium, through a mitral valve to a left ventricle, and through an aortic valve into an aorta, and then introducing the second end of the cable into the RLC at the femoral vein;
(b) securing an aortic valve therapeutic device to the first end of the cable; and
(c) pushing the aortic valve therapeutic device from the femoral vein while pulling the second end of the cable from the femoral artery to advance the aortic valve therapeutic device to the aortic valve site.

11. The method of claim 10, wherein step (a) includes:
positioning an expandable balloon of a balloon catheter in the right atrium and passing the balloon through the interatrial septum into the left atrium;

inflating the balloon within the left atrium, causing the balloon catheter to be carried by blood flow into and through the aorta to the femoral artery;
introducing the RLC over a proximal end of the balloon catheter;
advancing the RLC over the balloon catheter to position a distal end of the RLC in the left femoral artery;
introducing the second end of the cable into the RLC at the femoral vein, and advancing the second end of the cable to the distal end of the RLC;
capturing the second end of the cable via the femoral artery and positioning the second end external to the body.

12. The method of claim 10, wherein the step of capturing the second end includes advancing a snare into the vasculature via the left femoral artery and engaging the second end of the cable using the snare.

13. The method of claim 10, further including:
providing a left ventricle redirector (LVR) having a tubular lumen, a distal end actively steerable to form a curve;
passing the distal end of the lumen of the LVR over the second end of the cable at the femoral artery and into contact with the RLC;
advancing the LVR though the aorta and aortic valve to the left ventricle while simultaneously withdrawing the RLC while maintaining force between the LVR and RLC;
actively forming a curve in the distal end of the LVR within the left ventricle;
after positioning the LVR in the left ventricle, withdrawing the RLC from the vasculature.

14. The method of claim 13, further including:
after advancing the aortic valve therapeutic device over the cable, engaging a distal nose of the aortic valve therapeutic device with the distal end of the LVR;
seating an edge of the curve of the LVR within the apex of the left ventricle; and
during the step of pushing the aortic valve therapeutic device from the femoral vein, applying a force to the LVR from the femoral artery to press the curve into the apex of the left ventricle.

15. The method of claim 10, wherein the aortic valve therapeutic device is an aortic valve delivery system carrying a replacement aortic valve.

16. A method of delivering an aortic valve therapeutic device to an aortic valve site, comprising the steps of:
percutaneously introducing a cable into a vasculature of a patient and positioning the cable to run from a femoral vein, through the heart via a transeptal puncture, and to a femoral artery, the positioned cable extending out of the patient via said femoral vein and said femoral artery;
passing an aortic valve therapeutic device over a first end of the cable;
providing a left ventricle redirector (LVR) having a tubular lumen and a distal end actively steerable to form a curve;
passing the distal end of the lumen of the LVR over a second end of the cable, the second end opposite to the first end;
advancing the LVR to a left ventricle, actively forming the curve in the LVR and seating an edge of the curve of the LVR within an apex of the left ventricle;

pushing the aortic valve therapeutic device from its proximal end while pulling the second end of the cable to advance the aortic valve therapeutic device to the aortic valve site;

actively steering the distal end of the LVR as the aortic valve therapeutic device advances to the aortic valve site; and while pushing the aortic valve therapeutic device, applying a force to a proximal end of the LVR to press the curve into the apex of the left ventricle.

17. The method of claim 16, wherein applying the force to the LVR orients a distal nose of the aortic valve therapeutic device inferiorly and towards the patient's left.

18. The method of claim 16, wherein applying the force to the LVR prevents migration of the LVR into valve leaflets of a mitral valve.

19. The method of claim 16, further including engaging a distal nose of the aortic valve therapeutic device with the distal end of the LVR by:

providing a tubular connector having a distal end and a proximal end;

inserting the distal nose of the aortic valve therapeutic device AVTD into the proximal end of the tubular connector;

causing the distal end of the tubular connector to pass into the distal end of the LVR.

20. The method of claim 16, wherein the aortic valve therapeutic device is an aortic valve delivery system carrying a replacement aortic valve.

21. The method of claim 16, wherein the method includes introducing a right-to-left conduit (RLC) from the femoral vein into an inferior vena cava into a right atrium, through an interatrial septum into a left atrium, through a mitral valve to the left ventricle, and through an aortic valve into an aorta, and wherein the step of introducing the cable includes introducing the first or second end of the cable into the RLC at the femoral vein.

22. The method of claim 21, wherein:

the method includes:

positioning an expandable balloon of a balloon catheter in the right atrium and passing the balloon through an interatrial septum into the left atrium;

inflating the balloon, causing the balloon catheter to be carried by blood flow through the aorta to the femoral artery;

introducing the RLC over a proximal end of the balloon catheter;

advancing the RLC over the balloon catheter to position a distal end of the RLC in the femoral artery; and step (c) includes:

advancing the cable to the distal end of the RLC, capturing said cable via the femoral artery and pulling the cable from the femoral artery to draw a portion of the cable to a position external to the body.

23. The method of claim 22, wherein the step of capturing the cable includes advancing a snare into the vasculature via the left femoral artery and engaging the cable using the snare.

* * * * *